US006455682B1

(12) United States Patent
Barron

(10) Patent No.: US 6,455,682 B1
(45) Date of Patent: Sep. 24, 2002

(54) DNA MOBILITY MODIFIER

(75) Inventor: Annelise Barron, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 09/488,472

(22) Filed: Jan. 20, 2000

Related U.S. Application Data

(60) Provisional application No. 60/116,788, filed on Jan. 20, 1999, now abandoned.

(51) Int. Cl.$^7$ .................. C07H 19/00; C07H 21/00; C07H 21/02; C12Q 1/68

(52) U.S. Cl. .................. 536/23.1; 435/6; 435/91.1; 435/91.2; 536/24.3; 536/25.3

(58) Field of Search .................. 435/6, 91.1, 91.21; 536/23.1, 24.3, 25.3

(56) References Cited

U.S. PATENT DOCUMENTS

| 4,755,285 A | * | 7/1988 | Weckman et al. ........ 209/166 |
| 5,705,333 A | | 1/1998 | Shah et al. .............. 435/6 |

FOREIGN PATENT DOCUMENTS

| WO | WO 94/06451 | * | 3/1994 |
| WO | WO 94/25477 | | 11/1994 |

OTHER PUBLICATIONS

Ronald N. Zuckermann et al.; Efficient Method for the Preparation of Peptoids [Oligo (N–substituted glycines)] by Submonomer Solid–Phase Synthesis; Journal of American Chemical Society; 1992; vol. 114; pp. 10646–10647.

Jaan Noolandi; A new concept for sequencing DNA by capillary electrophoresis; Electrophoresis; 1992; vol. 13; pp. 394–395.

Ronald N. Zuckermann et al.; Discovery of Nanomolar Ligands for 7–Transmembrane G–Protein–Coupled Receptors from a Diverse N–(Substituted) glycine Peptide Library; J. Med. Chem.; 1994; vol. 37; pp. 2678–2685.

Pascal Mayer et al.; Theory of DNA Sequencing Using Free–Solution Electrophoresis of Protein–DNA Complexes; Anal. Chem.; 1994; vol. 66; pp. 1777–1780.

(List continued on next page.)

*Primary Examiner*—Jezia Riley
(74) *Attorney, Agent, or Firm*—Marshall, Gerstein & Borun.

(57) ABSTRACT

Polyamides comprising at least one hydrophilic $C_1$–$C_{10}$ hydrocarbyl substituent on an amide nitrogen atom, and methods for producing and using the same is provided. In particular, polyamides of the formula:

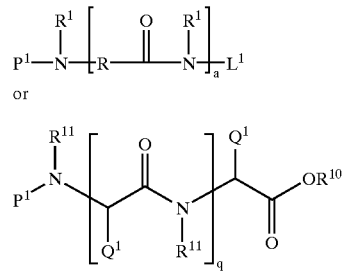

and methods for using the same for altering the ratio of charge/translational frictional drag of binding polymers to allow electrophoretic separation of polynucleotides or analogs thereof in a non-sieving liquid medium is provided, where a, q, $L^1$, $P^1$, $Q^1$, R, $R^1$, $R^{10}$ and $R^{11}$ are those described herein.

14 Claims, 14 Drawing Sheets

Peptide:

Peptoid:

OTHER PUBLICATIONS

A.R. Völkel et al.; Mobilities of Labeled and Unlabeled Single–Stranded DNA in Free Solution Electrophoresis; Macromolecules; 1995; vol. 28; pp. 8182–8189.

Didier Long et al.; Electrophoretic mobility of composite objects in free solution: Application to DNA separation; Electrophoresis; 1996 vol. 17; pp. 1161–1166.

Gianine M. Figliozzi et al.; Synthesis of N–Substituted Glycine Peptoid Libraries; Method in Enzymology, vol. 267; 1996; pp. 437–447.

Gary W. Slater et al.; Recent developments in DNA electrophoretic separations; Electrophoresis; 1998; vol. 19; pp. 1525–1541.

Christoph Heller et al., Free–solution electrophoresis of DNA; Journal of Chromatography A; 1998; vol. 806; pp. 113–121.

Hongji Ren et al.; Separating DNA sequencing fragments without a sieving matrix; Electrophoresis; 1999; vol. 20; pp. 2501–2509.

Noble et al.; "Impact of Biophysical Parameters on the Biological Assessment of Peptide Nucleic Acids, Antisense Inhibitors of Gene Expression"; *Drug Development Research;* 1995; 34; pp. 184–195.

Christensen et al., "Solid–Phase Synthesis of Peptide Nucleic Acids"; *Journal of Peptide Science;* 1995; vol. 3; pp. 175–183.

Burgess et al.; "Solid Phase Syntheses of Oligoureas"; *J. Am. Chem. Soc.;* 1997; 119; pp. 1556–1564.

* cited by examiner

Peptide:

Peptoid:

Polypeptide with reactive amino sidechains

+ peptoid oligomers

+ condensation reagents such as HATU and DIEA

'bottle-brush'-type polypeptide-peptoid conjugate

DNA MOBILITY MODIFIER

CROSS-REFERENCE TO RELATED APPLICATION

This application claims the benefit of provisional U.S. patent application Ser. No. 60/116,788, filed Jan. 20, 1999, now abandoned.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. DE-FR02-99ER62789 awarded by Department of Energy.

FIELD OF THE INVENTION

The present invention relates to a composition for modifying the mobility of DNA in a sieving or non-sieving matrix, and to methods of using the composition for determining the sequence of a target polynucleotide.

BACKGROUND OF THE INVENTION

Miniaturized electrophoresis systems have the potential to substantially increase the speed and throughput of automated DNA sequencing while reducing the overall cost per base. Current miniaturized electrophoresis systems, in particular capillary electrophoresis, continue to rely upon the use of viscous polymer solutions as "gels" that provide a physical separation of DNA fragments according to chain length.

Unfortunately, gel-based methods for DNA sequencing have a maximum read lengths of about 1000 bases, with a typical read length being at most about 550 to about 650 bases. Since engineered DNA polymerases can produce more than 2500 bases of sequence per Sanger sequencing reaction, even optimized sequencing gels essentially "hide" or "lose" about 1500 bases of information per reaction. Moreover, the replacement of viscous polymer gels from chip microchannels is difficult, if not impossible, thus preventing the use of automated chip-based gel electrophoresis systems for multiple, consecutive DNA sequencing analysis.

In addition to the above-described read-length limitations of gel electrophoresis, there is another drawback to the use of gels that makes them particularly inconvenient for capillary and microchip geometries. A reusable sequencing chip or capillary array must allow gels to be replaced before each run to eliminate sample carry-over and avoid irreproducibilities and current failures that may result from chemical- and/or field-induced gel breakdown. Unfortunately, no replaceable, high-performance sequencing gel appropriate for the microchannels on CE chips is currently available. And since sequencing gels cannot be replaced from chip microchannels, each chip is essentially a single-use device, an outcome that will greatly increase associated operating costs and decrease the convenience of miniaturized DNA sequencers.

Moreover, the sequencing gels used in experimental microchips currently are typically polymerized in situ, which typically yields low-performance gels because acrylamides generally do not polymerize to high molecular weights or yield greater than 85% conversion, i.e., polymerization, in a confined microchannel. While extremely "large" channels may be fabricated onto the chip (e.g., 100 μm wide×90 μm deep), which allows viscous gels to be forced into the channels under pressure, these large channels, however, result in broadened DNA bands and/or reduced separation efficiency.

Therefore, there is a need for a method for electrophoretic DNA sequencing that does not demand the use of high-viscosity physical gels or cross-linked chemical gels. There is also a need for novel sequencing technologies that will substantially increase the speed and throughput of automated sequencing instruments while reducing the overall cost per base.

SUMMARY OF THE INVENTION

The present invention provides a compound and methods for using the same in electrophoretic separation of binding polymers. In particular, the present invention provides a polyamide compound comprising at least one hydrophilic $C_1$–$C_{10}$ hydrocarbyl substituent on an amide nitrogen atom and methods for using the polyamide in electrophoretic separation of binding polymers in a non-sieving liquid medium.

One aspect of present invention provides a polyamide of the formula:

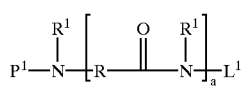

where $L^1$ is selected from the group consisting of H, amide protecting groups and moieties of the formula:

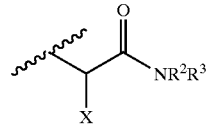

and

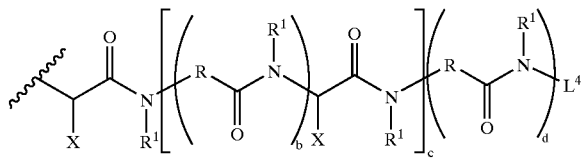

each X is independently an amino acid side-chain residue or a moiety of the formula —$CH_2SL^2$ or —$(CH_2)_3NL^3R^4$;

each $L^2$ is independently a thiol protecting group or a moiety of the formula:

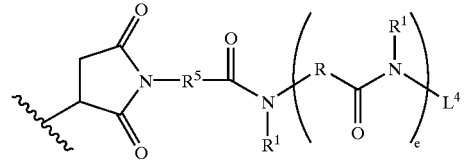

each $L^3$ is independently H, an amine protecting group, an α,β-unsaturated carbonyl moiety or a conjugate moiety of the formula:

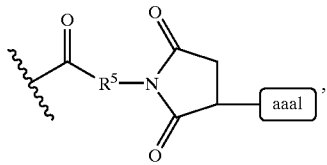

provided at most one and only one $L^3$ is the conjugate moiety;
each $L^4$ is independently H, amide protecting groups or the moiety of the formula:

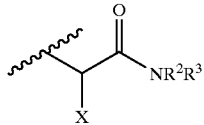

each R is independently —$CH_2$— or

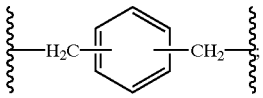

each $R^1$ is independently H, a protecting group or $C_1-C_{10}$ hydrocarbyl;
each of $R^2$ and $R^3$ are independently H, $C_1-C_6$ alkyl, or an amide protecting group;
each $R^4$ is independently H, an amine protecting group, or $C_1-C_6$ alkyl, provided at least one of $L^3$ or $R^4$ on the same nitrogen atom is not H;
each $R^5$ is independently $C_1-C_{10}$ alkylene;
aaa1 is the polynucleotide moiety;
$P^1$ is H, $C_1-C_6$ alkyl or an amine protecting group;
a is an integer from 1 to 200;
each b is independently an integer from 1 to 200;
c is an integer from 1 to 10;
d is an integer from 1 to 50; and
each e is independently an integer from 1 to 200.

Preferably, for polyamide of formula I, at least one $R^1$ is hydrophilic $C_1-C_{10}$ hydrocarbyl.

Another aspect of the present invention provides a polyamide of the formula:

II

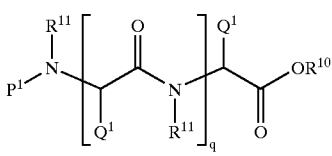

where
each $R^{10}$ is independently H or a carboxylic acid protecting group;
each $R^{11}$ is independently H, a protecting group or $C_1-C_{10}$ hydrocarbyl;
q is an integer from 1 to 1,200; and
each $Q^1$ is independently an amino acid side-chain residue or a derivative thereof, provided at least one $Q^1$ is an amino acid side-chain residue derivative of the formula:

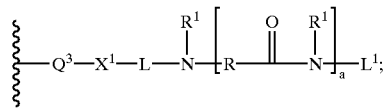

each of the moiety —$Q^3$—$X^1$— is an amino acid side-chain residue having —$X^1$H functional group;
each $X^1$ is independently O, S or $NP^2$;
L is a linker comprising $C_1-C_6$ alkylene with carbonyl groups on both of the terminal groups; and
each of $L^1$, $L^2$, $L^3$, $L^4$, $P^1$, R, $R^1$, $R^2$, $R^3$, $R^4$, $R^5$, X, a, b, c, d, and e is independently those described above.

Another embodiment of the present invention provides a polyamide-polynucleotide primer conjugate and method for determining the nucleotide sequence of a target nucleic acid which comprises the steps of:

(a) annealing a polyamide-polynucleotide primer conjugate to the target nucleic acid, wherein the polyamide moiety comprises at least one hydrophilic $C_1-C_{10}$ hydrocarbyl substituent on an amide nitrogen atom;

(b) extending the primer with a nucleic acid polymerase in the presence of nucleoside triphosphate precursors and at least one chain terminating nucleotide, thereby forming conjugated nucleic acid fragments;

(c) separating the conjugated nucleic acid fragments by electrophoresis in a non-sieving matrix; and (d) determining the nucleotide sequence of the target nucleic acid by the separated nucleic acid fragments.

Preferably, the polyamide-polynucleotide primer conjugate comprises a thioether linkage between a polyamide moiety and a polynucleotide moiety. Preferably, the polyamide-polynucleotide primer conjugate is a polypeptoid-polynucleotide primer conjugate of formula I or polypeptide-polynucleotide primer conjugate of formula II above comprising at least one $L^3$ where one and only one $L^3$ is the conjugate moiety of the formula:

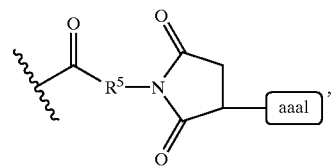

where aaa1 is the polynucleotide moiety, wherein the hydroxy group of the terminal 5'-position of the polynucleotide moiety has been replaced with a thiol group to form the thioether linkage between the polyamide moiety and the polynucleotide moiety.

Another embodiment of the present invention provides a method for producing a polyamide of the formula:

III

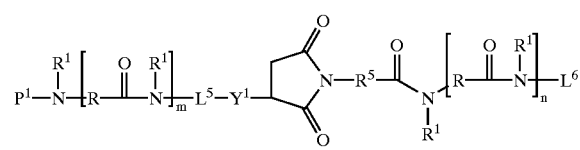

comprising contacting a nucleophilic compound of the formula:

IV with an α,β-unsaturated carbonyl of the formula:

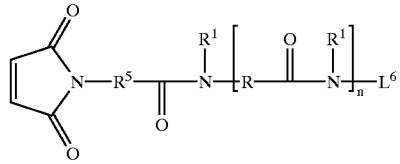

V under conditions sufficient to produce the polyamide III, where $L^5$ is a moiety of the formula:

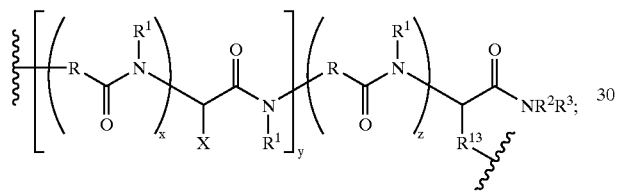

$L^6$ is a moiety of the formula:

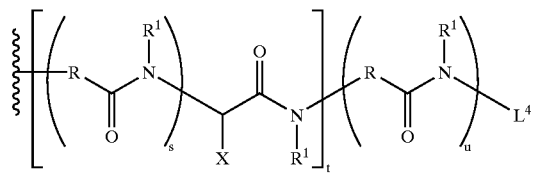

$Y^1$ is S or $NP^2$;

each $P^2$ is independently H, $C_1-C_6$ alkyl or an amine protecting group;

each $R^{13}$ is $C_1-C_6$ alkylene;

m is an integer from 1 to 200;

n is an integer from 1 to 200;

x is an integer from 0 to 200;

y is an integer from 0 to 10;

z is an integer from 0 to 50;

s is an integer from 0 to 200;

t is an integer from 0 to 10;

u is an integer from 0 to 50; and each of $L^2$, $L^3$, $L^4$, $P^1$, R, $R^1$, $R^2$, $R^3$, $R^4$, X, and e is is independently those described above.

Still another embodiment of the present invention provides a method for producing a polyamide of the formula:

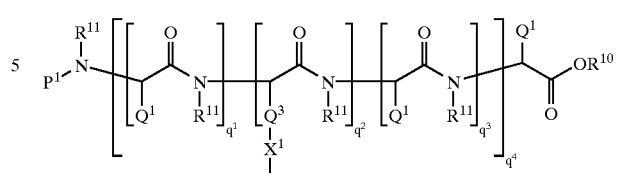

VI comprising contacting a polypeptide of the formula:

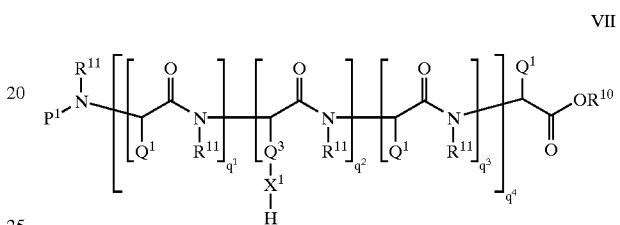

VII with a polypeptoid of the formula:

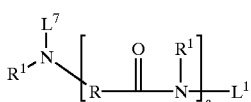

VIII under conditions sufficient to produce polyamide VI, where $L^7$ is a moiety of the formula $—C(=O)—R^{12}—C(=O)OM$;

M is H or a metal;

each $q^1$ is independently an integer from 0 to about 40;

each $q^2$ is independently an integer from 1 to about 40;

each $q^3$ is independently an integer from 0 to about 40;

$q^4$ is an integer from 1 to about 50;

L is as described above, preferably a moiety of the formula $—C(=O)—R^{12}—C(=O)—$;

$R^{12}$ alkylene; and each of $L^1$, $L^2$, $L^3$, $L^4$, $P^1$, $Q^1$, the moiety $—Q^3—X^1—$, R, $R^1$, $R^2$, $R^3$, $R^4$, $R^5$, $R^{10}$, $R^{11}$, X, $X^1$, a, b, c, d, and e is independently those described above.

Still yet another embodiment of the present invention provides a method for forming a bond between a fused silica surface and a polyamide comprising:

(a) contacting the surface of said fused silica with an oxidizing agent to form an oxidized surface comprising a hydroxy group;

(b) silanizing the oxidized surface of the fused silica with a silanizing agent to form a silanized surface;

(c) contacting the silanized surface with a linking reagent to form a surface having silanized linker; and (d) contacting the silanized linker with the polyamide to form a covalent bond between the silanized linker and the polyamide.

In one particular aspect of bond formation between the fused silica surface and the polyamide, the polyamide is a polypeptoid of the formula:

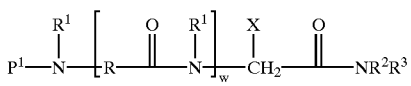

which forms the covalent bond between the fused silica and the functional group X,
where
each of $P^1$, $R^1$, $R^2$ and $R^3$ is independently those described above;
X is as described above, preferably —$CH_2SH$ or —$(CH_2)_3NHR^2$; and
w is an integer from 1 to 200.

In another aspect of bond formation between the fused silica surface and the polyamide, the polyamide is a polypeptide of formula II above provided the polypeptide comprises at least one X which forms the covalent bond between the fused silica and the functional group X.

DETAILED DESCRIPTION OF THE INVENTION

Figure 1:
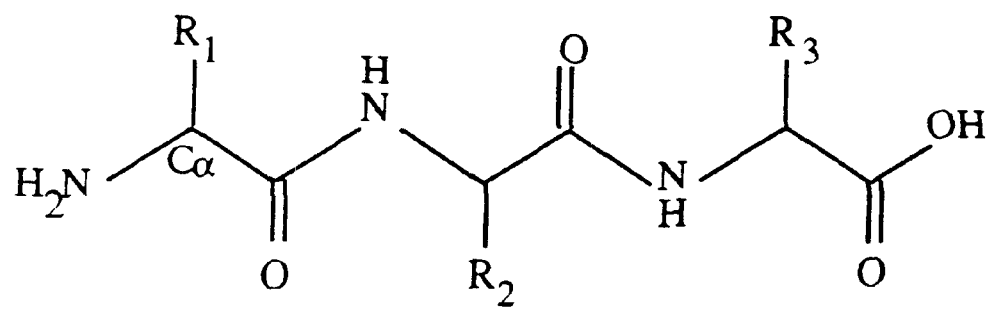
FIG. 1 is a comparison of the structures of a tripeptide and a tripeptoid.
Figure 1:
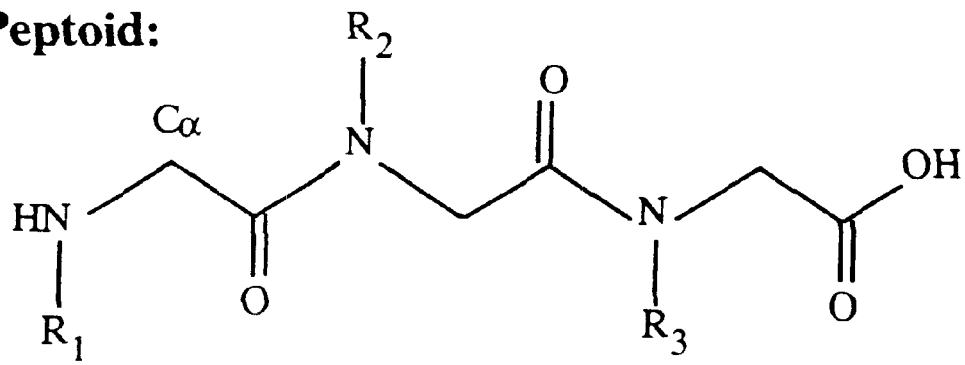

A "non-sieving matrix" means a liquid medium which is substantially free of a mesh or network or matrix of interconnected or physically entangled polymer molecules.

A "sieving matrix" means a liquid medium which contains a mesh or network or matrix of interconnected or physically entangled polymer molecules.

The "translational frictional drag" of a polymer is a measure of the polymer's frictional drag as it moves electrophoretically through a defined, non-sieving or sieving liquid medium.

The "charge" of a polymer is the total net electrostatic charge of the polymer at a given pH.

A "target polynucleotide" may include one or more nucleic acid molecules, including linear or circularized single-stranded or double-stranded DNA or RNA molecules.

"Target nucleic acid sequence" means a contiguous sequence of nucleotides in the target polynucleotide. A "plurality" of such sequences includes two or more nucleic acid sequences differing in base sequence at one or more nucleotide positions.

A "sequence-specific binding polymer" or a "binding polymer" means a polymer effective to bind to one target nucleic acid or subset sequence of the target nucleic acid with base-sequence specificity, and which has a substantially lower binding affinity, under selected hybridization conditions, to any other target sequence or sequence subset in a given plurality of sequences in a test sample.

A "drag-tag" refers to a compound or a moiety which when linked to a binding polymer, changes the electrophoretic mobility of the binding polymer.

A "distinctive ratio of charge/translational frictional drag" of a drag-tag is evidenced by a distinctive, i.e., unique, electrophoretic mobility of the drag-tag in a non-sieving medium. "Hydrocarbyl" groups are moieties having carbon atom chains. Such groups include alkyl, aryl, arylalkyl, alkylaryl, alkylarylakyl, cycloalkyl, alkylcycloalkyl, cycloalkylalkyl and alkylcycloalkylalkyl. It should be appreciated that some or all of the hydrogen in hydrocarbyl may be replaced with one or more types of halide groups such as fluoro, chloro, bromo or iodo groups. The carbon chain in a hydrocarbyl group may be a straight chain or a branched chain. Moreover, hydrocarbyl group may be substituted with one or more heteroatoms such as oxygen, phosphorous, nitrogen, sulfur or combinations thereof.

"Alkyl" groups according to the invention are aliphatic hydrocarbons which can be straight or branched chain groups having a number of indicated carbon atoms. Alkyl groups optionally can be substituted with one or more substituents, such as halo, aryl, hydroxy, alkoxy, carboxy, oxo and cycloalkyl. There may be optionally inserted along the alkyl group one or more oxygen, sulfur or substituted or unsubstituted nitrogen atoms. Exemplary alkyl groups include methyl, ethyl, i-propyl, n-butyl, t-butyl, n-pentyl, heptyl, hexyl, trifluoromethyl, trichloromethyl, and octyl.

As used in this invention, a structure with a terminating bond without any specific atom identification refers to a point of connection, for example, a description "a compound R—X where X is a moiety of —Ph" means that Ph (i.e., a phenyl group) is attached to the R group, i.e., the compound being referred to is R—Ph. Alternatively, a point of connection may be indicated by a wavy line across the bond where the connection is present.

The terms "substituted," "substituted derivative" and "derivative" when used to describe a chemical moiety means that at least one hydrogen bound to the unsubstituted chemical moiety is replaced with a different atom or a chemical moiety.

Figure 2:
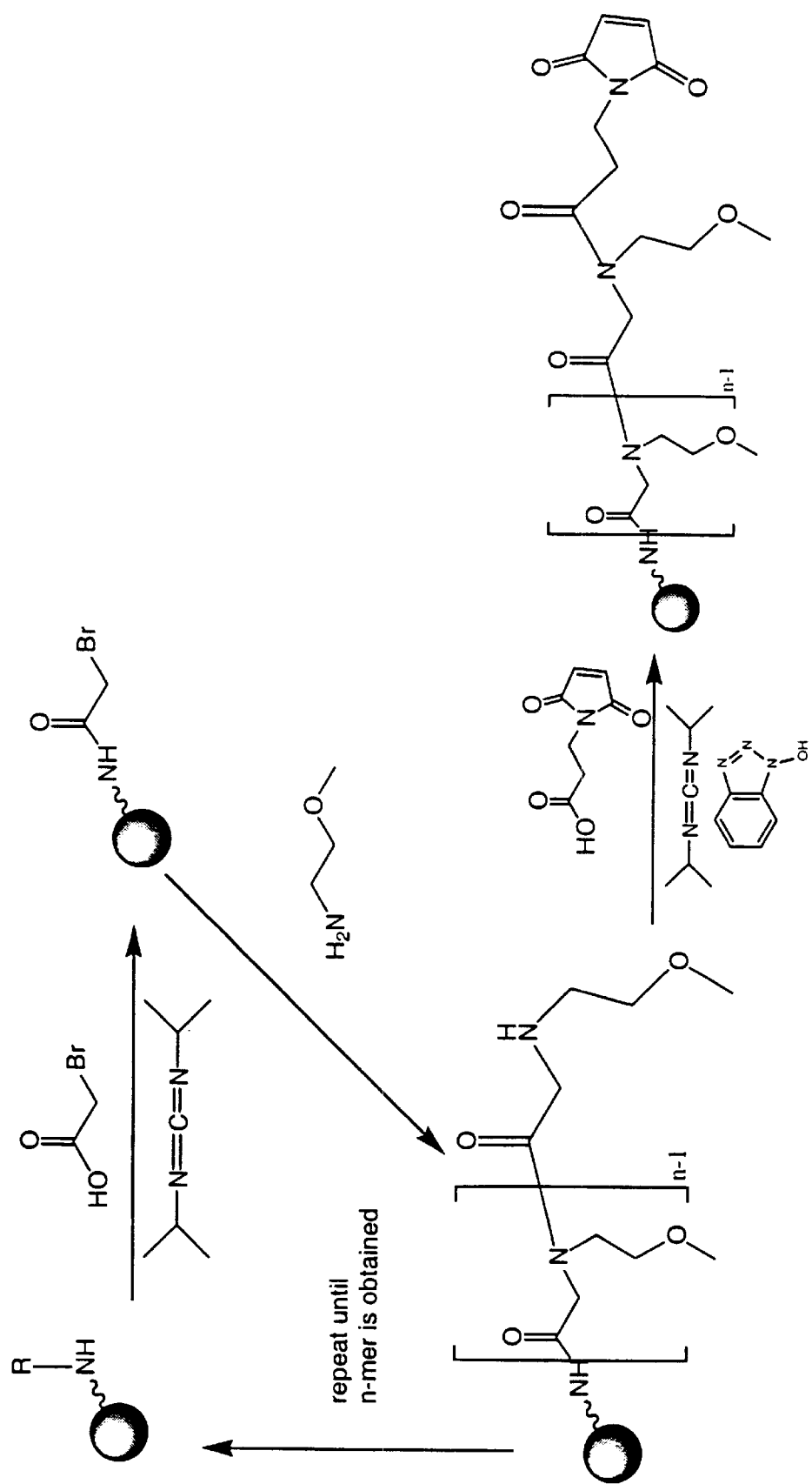
FIG. 2 is a schematic illustration of a sub-monomer synthesis of a polyamide of the present invention.

The term "peptoid" refers to a polyamide having one or more substituent on the amide nitrogen atom. A peptoid is a synthetic analog of a peptide with the difference being that while a side-chain residue on a peptide is attached to a carbon atom α- to the carbonyl group, in a peptoid the "side-chain residue", is attached to the amide nitrogen atom. An exemplary "polypeptoid" is a poly-(N-substituted glycine) compound. These peptidomimetic molecules (i.e., polypeptoids) have a number of particular advantages as discussed below. For example, peptoids are synthetic polymers with controlled sequences and lengths, that can be made by automated solid-phase organic synthesis to include a wide variety of side-chains having different chemical functions. Peptoids have a number of notable structural features in comparison to peptides. For example, whereas the side-chain ("R") groups on biosynthetically produced peptides must be chosen from among the 20 amino acids, peptoids can include a wide variety of different, non-natural side-chains because in peptoid synthesis the R group can be introduced as a part of an amine or by alkylation of the amine or the amide nitrogen, e.g., see FIG. 2. This is in contrast to synthetic peptides for which the incorporation of non-natural side-chains requires the use of non-natural α-protected amino acids. Polypeptoids can be synthesized in a sequence-specific fashion using an automated solid-phase protocol, e.g., the sub-monomer synthetic route. See, for example, Wallace et al., Adv. *Amino Acid Mimetics Peptidomimetics*, 1999, 2, 1–51 and references cited therein, all of which are incorporated herein in their entirety by this reference. Generally, when attached to a binding polymer, longer polypeptoids provide a higher ratio of charge/translational frictional drag (i.e., α value), than shorter polypeptoids. The synthesis of long polypeptoids can be achieved using the sub-monomer protocol. For example, using the methods disclosed herein, polypeptoids of 20 mer, 40 mer, and 60 mer polypeptoids with alternating methoxy and benzyl side chains have been readily synthesized.

The terms "amino acid side-chain residue" and "amino acid side-chain" refer to the "R" group in an amino acid which is generally written as $HO_2CCH(R)NH_2$. For example, R is H for glycine and methyl for alanine. In proline, one of the H groups in the —$NH_2$ substituent is replaced by the —$CH_2$— moiety of the R group, i.e., the "—$(CH_2)_3$—" moiety. The term "an amino acid side-chain derivative" refers to an amino acid side-chain which has been chemically modified. For example, the phenyl ring of the benzyl group in phenylalanine side-chain can be substituted with one or more of the following substituents: halide, hydroxy, alkoxy, amino, nitro, carboxy, alkyl, including trifluoromethyl, and other substituents which are apparent to one of ordinary skill in the art. Other examples of "an amino acid side-chain derivative" include, but are not limited to, arginine side-chain which has been modified such that the =NH group is replaced by a carbonyl (=O) group, methionine side-chain which has been oxidized to sulfonyl group (—$SO_2$—), and proline side-chain which has been functionalized, e.g., a moiety of the formula —$CH_2$—CH(OH)—$CH_2$—.

The present invention provides a compound and methods for sequencing a binding polymer. Preferably, the binding polymer is a polynucleotide or an analog thereof. In particular, the present invention provides a polyamide compound comprising at least one hydrophilic $C_1$–$C_{10}$ hydrocarbyl substituent on an amide nitrogen atom and methods for using the same. Hydrophilic groups can include $C_1$–$C_{10}$ hydrocarbyls having one or more heteroatom substituents which can participate in hydrogen bonding with one or more hydrogen atom donors and/or hydrogen atom acceptors. Such heteroatom substituents can include oxygen, nitrogen, sulfur, phosphorous, and mixtures thereof. Exemplary functional groups resulting from such heteroatom(s) include hydroxy groups, ethers, esters, amines, sulfoxides, sulfones, sulfonamides, phosphoamides, phosphates, phosphites, nitroso, nitro, hydroxy amines, nitrate and N-oxides. Specific examples of hydrophilic groups include alkyl thiols such as methythiol, (2'-thiol)ethyl, (3'-thiol)propyl, (4'-thiol) butyl, (2'-thiol)propyl, (3'-thiol)butyl and the like; amines such as aminomethyl, (2'-amino)ethyl, (3'-amino)propyl, (4'-amino)butyl, (2'-amino)propyl, (3'-thiol)butyl and the like, such alkyl amines may have one or more substituent or amino protecting group on the amino group; alkyl hydroxides such as hydroxy methyl, (2'-hydroxy)ethyl, (3'-hydroxy)propyl, (4'-hydroxy)butyl, (2'-hydroxy)propyl, (3'-hydroxy)butyl and the like; alkyl sulfones; alkyl sulfoxides; alkyl phosphates; alkyl phosphoamides, alkyl sulfonamides, and alkyl phosphites. Synthesis of polyamides of the present invention can be achieved using, for example, a commercial peptide synthesizer such as Perkin-Elmer Applied Biosystems 433A.

More particularly, the present invention provides a polyamide compound comprising a backbone chain which has one or more branch chains connected to the backbone chain. The backbone chain is selected from the group consisting of polypeptides, polypeptoids and peptide-peptoid chimera. As used herein, the term "peptide-peptoid chimera" refers to a copolymer of peptide and peptoid monomers. Typically, the backbone chain comprises at least about 100 monomers, preferably at least about 400 monomers, more preferably at least about 600 monomers, and most preferably at least about 1,200 monomers. In one particular embodiment of the present invention, the backbone chain comprises from about 100 monomers to about 1,200 monomers, more preferably from about 400 monomers to about 1,200 monomers, and most preferably from about 600 monomers to about 1,200 monomers. The backbone chain can be prepared synthethically using a currently-available peptide or peptoid synthesizer, or in case of a polypeptide it can be produced by microorganisms, preferably genetically engineered (i.e., gene modified) microorganisms, such as *E. Coli*. In this manner polypeptides of various lengths can be prepared, for example, by genetic engineering. Processes for producing polypeptides using gene modified microorganisms are well known to one of ordinary skill in the art, for example, such process are disclosed by McMillan et al., in "Rapid assembly of synthetic genes encoding protein polymers", *Macromolecules*, 1999, 32, 3643–3648; McGrath et al., in "Genetically directed syntheses of new polymeric materials. Expression of artificial genes encoding proteins with repeating -(AlaGly)$_3$ProGluGly- elements", *J. Am. Chem. Soc.*, 1992, 114, 727–733; and Prince et al., in "Constuction, cloning, and expression of synthetic genes encoding spider dragline silk", *Biochemistry*, 1995, 34, 10879–10885, which are incorporated herein by reference in their entirety.

The branch chain is selected from the group consisting of polypeptoids, and peptide-peptoid chimeras. It should be appreciated that a peptide-peptoid chimera can have any combination of amino acid(s) and peptoid(s). The branch chain can be linked to the backbone chain by one or more amino acids or other suitable linkers including compounds containing dicarbonyl functional groups. Preferably, the branch chain is a peptide-peptoid chimera moiety in which at least one of the amino acids present in the peptide-peptoid chimera serves as a linker. Preferably, the carbonyl group present in the side chain residue of aspartic acid or glutamic acid is used to link the peptide-peptoid chimera moiety to an amine or amide functional group present in the backbone chain.

The polyamide of the present invention can be straight chain, dendritic, branched, comb-like or mixtures thereof. While the branched chain can have one monomer, preferably it comprises from about 2 monomers to about 50 monomers, more preferably from about 2 monomers to about 30 monomers, and most preferably from about 6 monomers to about 20 monomers. It should be appreciated that when more than one branched chain is present in a backbone chain, the branched chains may comprise the same or different number of monomers. Preferably, polyamides of the present invention comprise at least about 25 branch chains, more preferably at least about 50 branch chains, and most preferably at least about 100 branch chains. However, the amount of branch chain moiety present in the polyamide of the present invention depends upon the α value of the drag-tagged nucleic acid needed for sequencing.

For polyamides comprising a polypeptide backbone chain with polypeptoid or polypeptide-polypeptoid chimera branch chains, polypeptoid or polypeptide-polypeptoid chimera is covalently bonded to the polypeptide backbone through the use of standard peptide condensation reagents such as N-[(dimethylamino-1H-1,2,3-triazol[4,5-b]pyridin-1-ylmethylene]-N-methyl methanaminium hexafluorophosphate N-oxide (HATU), with N,N-diisopropylethylamine (DIEA). The reaction between the HATU-activated peptoid carboxylate and the lysine ε-amino groups on the peptide backbone (as well as the free amino-terminus) yields the bottle-brush molecular architecture, where the peptoid side chains are linked to the polypeptide backbone by a peptide bond.

The peptide bond linkage can be formed using any of the currently known reactions between a carboxylate and an amino group, including reactions using currently known peptide condensation reagents. Exemplary reagents for such peptide bond linkage reactions include, but are not limited to, N,N'-diisopropyl carbodiimide (DIC); N-hydroxybenzotriazole (HOBt); DIFNA; N-[(1H-benzotriazol-1-yl)-dimethylamino methylene]-N-methylmethanaminium hexafluoro-phosphate N-oxide (HBTU); HATU; benzotrizole-1-yl-oxy-tris-(dimethylamino)-phosphonium hexafluorophosphate (BOP or Castrols reagent); 1,1'-carbonyldiimidazole (CDI); N,N'-dicyclohexyl carbodiimide (DCC); 4-dimethyl aminopyridine (DMAP); 2-ethoxy-1-ethoxycarbonyl-1,2-dihydroquinone (EEDQ); bromo-tris-pyrrolidino-phosphonium hexafluorophosphate (PyBroP); N-hydroxy-5-norbornene-endo-2,3-dicarboxyimide (HONB); and 1-ethyl-3-[3-dimethylaminopropyl]carbodiimide hydrochloride (EDC).

In one particular aspect, polyamides of the present invention are neutral (i.e., uncharged) water-soluble polyamides having at least about 150 residues (i.e., monomers or monomeric units) in length which contain one or more hydrophilic side chains, in essentially monodisperse preparation (i.e., all chains having the same molecular mass).

Figure 3:
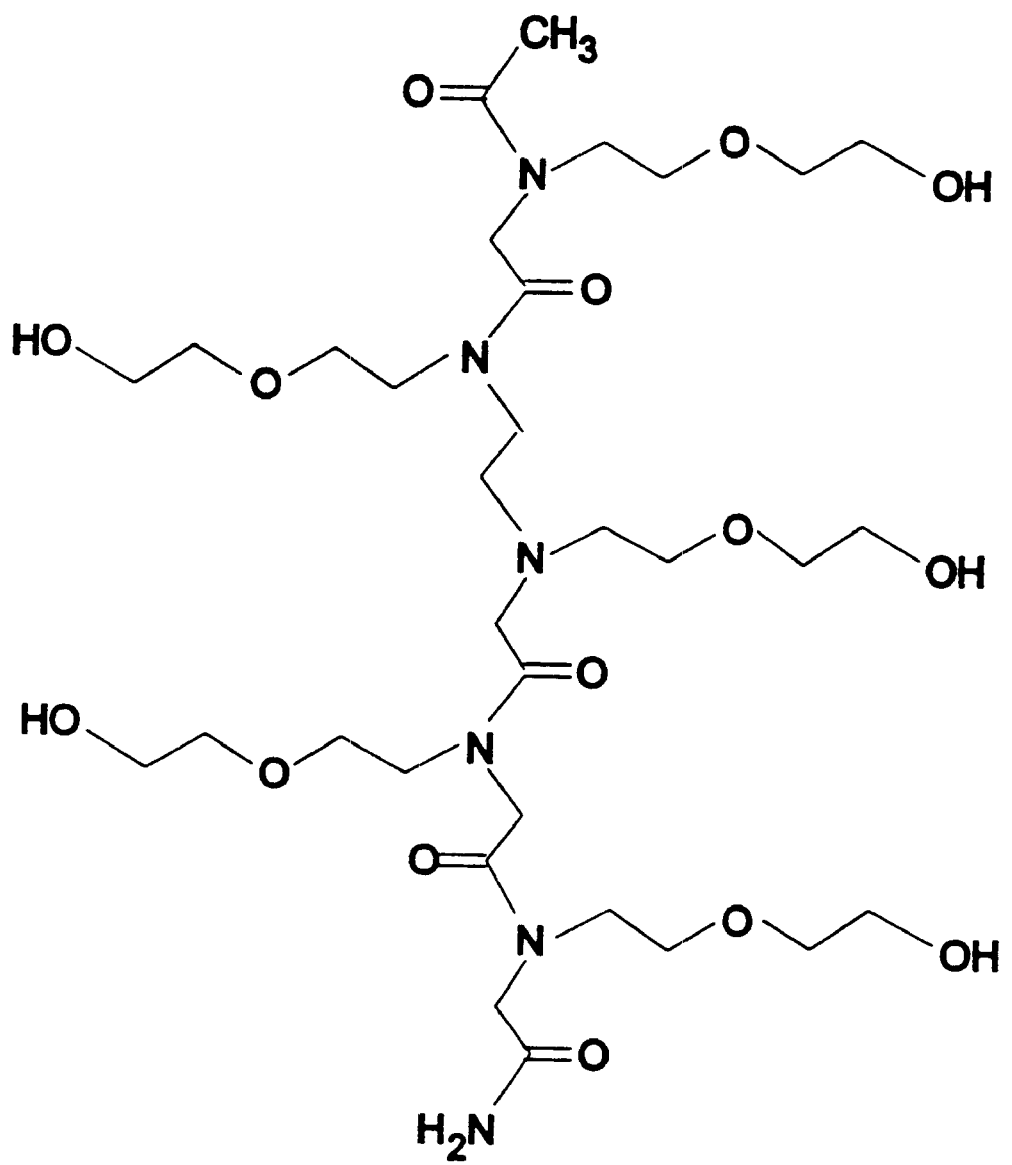
FIG. 3 is an illustration of 5-mer polyamides of the present invention with ethoxyethanol side chains.
Figure 5A:
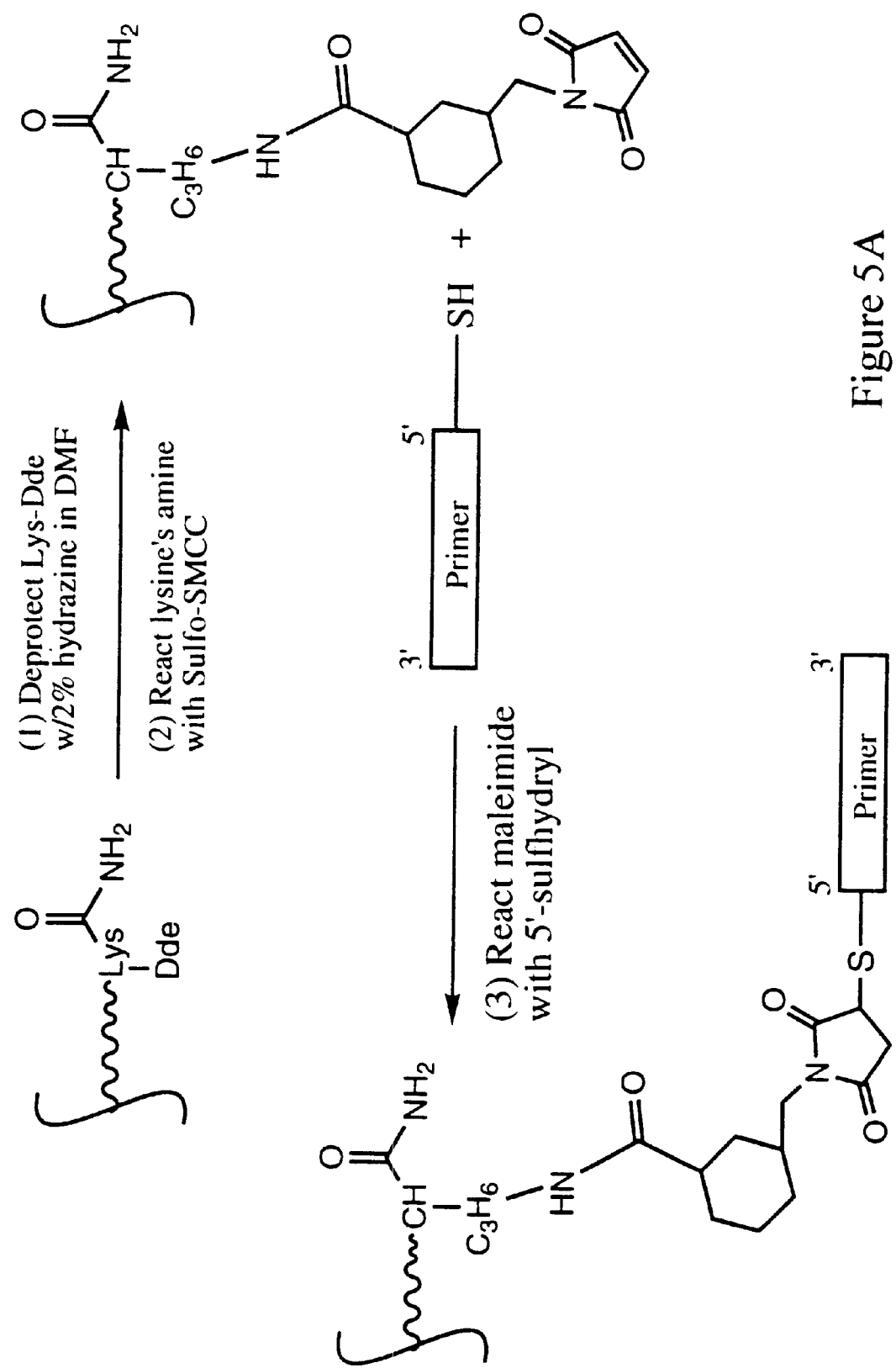
FIGS. 5A and 5B are schematic synthetic methods for linking polyamides of the present invention to a 5'-thiolated primer.

Two or more polyamides can be linked "end-to-end" to create longer polyamides. In addition, other approaches can be used to create novel molecular architectures (such as "bottle-brush" graft co-polymers) to increase the α value of these molecules. Preferably, polyamides of the present invention have α values of at least about 50, more preferably at least about 75, and most preferably at least about 100. As shown in FIG. 5, one method for producing such polyamides having a high α value is covalently linking a backbone chain with one or more branch chains using, for example, coupling agents such as Sulfo-SMCC coupling. Covalent bond formation of suitable length polypeptoid side chains onto a backbone chain that has been designed with a number of properly-spaced cysteine, or preferably lysine (not shown), side-chain residues in its backbone is shown in FIG. 5. By following the synthetic strategies outlined in FIG. 5, synthesis of polyamides that resemble a "bottle-brush" is achieved. It is believed that "bottle-brush" polyamides engender a large amount of frictional drag, that significantly exceeds the drag engendered by a linear polyamide chain that is illustrated in FIG. 3.

One particular embodiment of the present invention is a polypeptoid compound of the formula:

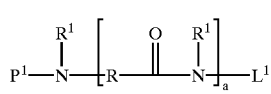

IA where $L^1$ is selected from the group consisting of H, amide protecting groups and moieties of the formula:

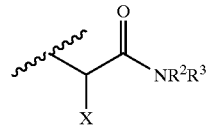

and

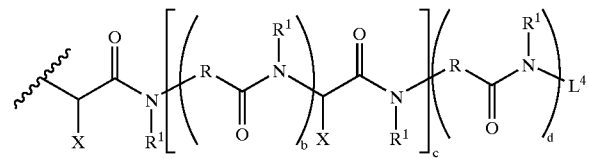

each X is independently an amino acid side-chain residue or a moiety of the formula $—CH_2SL^2$ or $—(CH_2)_3NL^3R^4$;

each $L^2$ is independently a thiol protecting group or a moiety of the formula:

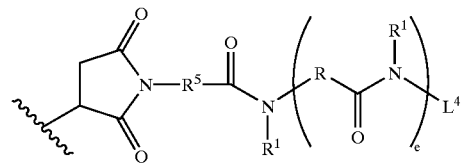

each $L^3$ is independently H, an amine protecting group or an α,β-unsaturated carbonyl moiety;

each $L^4$ is independently H, amide protecting groups or the moiety of the formula:

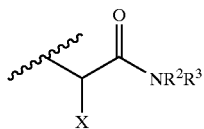

each $R^4$ is independently H, an amine protecting group, or $C_1$–$C_6$ alkyl, provided at least one of $L^3$ or $R^4$ on the same nitrogen atom is not H; and each of $P^1$, R, $R^1$, $R^2$, $R^3$, $R^5$, a, b, c, d, and e is independently those described in the Summary of the Invention section.

Another embodiment of the present invention is a polypeptide compound of the formula:

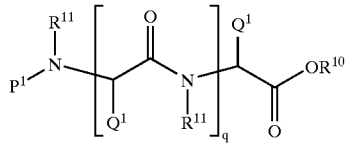

IIA where each $Q^1$ is independently an amino acid side-chain residue or a derivative thereof, provided at least one $Q^1$ is an amino acid side-chain residue derivative of the formula:

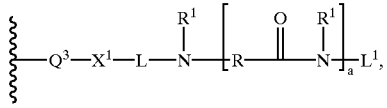

each of the moiety —$Q^3$—$X^1$— is an amino acid side-chain residue having —$X^1$H functional group;

each $X^1$ is independently O, S or $NP^2$;

each $L^1$ is independently H, amide protecting group or a moiety of the formula:

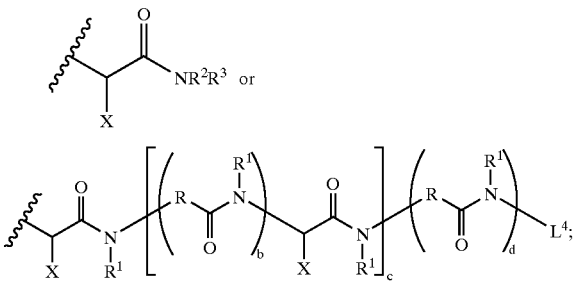

a moiety of the formula —$CH_2SL^2$ or —$(CH_2)_3NL^3R^4$;

each $L^2$ is independently a thiol protecting group or a moiety of the formula:

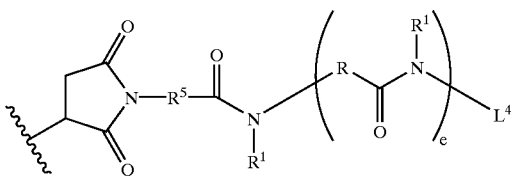

each $L^3$ is independently H, amine protecting groups or an α,β-unsaturated carbonyl moiety;

each $L^4$ is independently H, amide protecting groups or the moiety of the formula:

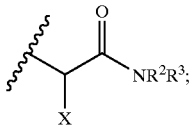

each $R^4$ is independently H, an amine protecting group, or $C_1$–$C_6$ alkyl, provided at least one of $L^3$ or $R^4$ on the same nitrogen atom is not H;

each of L, $P^1$, R, $R^1$, $R^2$, $R^3$, $R^5$, $R^{10}$, $R^{11}$, a, b, c, d, e, and q is independently those described in the Summary of the Invention section.

As discussed above, polypeptides of the present invention can be produced synthetically or using genetically modified microorganisms. In one particular embodiment of the present invention, the polypeptide backbone chain is produced by a genetically modified microorganism, such as E. coli. Polypeptides thus produced contain a predetermined number of lysines within the peptide chain. In one aspect of the present invention, these lysine moieties in the polypeptide are then attached to branch chains comprising polypeptoids which contain at least one aspartic acid, glutamic acid, or N-substituted peptoids containing a carboxylate moiety on the N-substituent. Formation of a covalent bond between these amino acid carboxylic side chains and the amide, or preferably an amine, nitrogen of the polypeptide provides a compound of formula IIA.

Still yet another embodiment of the present invention provides a polyamide-polynucleotide primer conjugate of the formula:

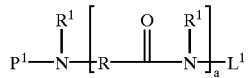

IB where $L^1$ is a moiety of the formula:

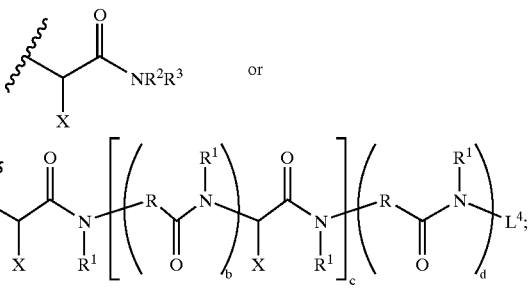

each X is independently an amino acid side-chain residue or a moiety of the formula —$CH_2SL^2$ or —$(CH_2)_3NL^3R^4$;

each $L^2$ is independently a thiol protecting group or a moiety of the formula:

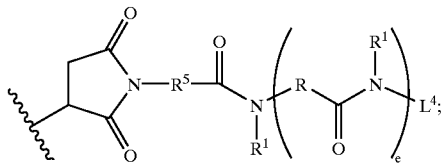

each $L^3$ is independently H, an amine protecting group or a conjugate moiety of the formula:

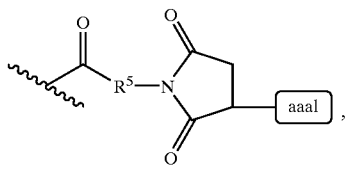

provided one and only one $L^3$ is the conjugate moiety;

$L^4$ is a moiety of the formula:

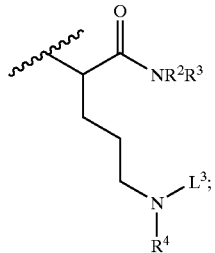

each $R^1$ is independently H, a protecting group or $C_1$–$C_{10}$ hydrocarbyl, provided at least one $R^1$ is hydrophilic $C_1$–$C_{10}$ hydrocarbyl;

$R^4$ is H, an amine protecting group, or $C_1$–$C_6$ alkyl, provided at least one of $L^3$ and $R^4$ is not H;

is aaa1 is the polynucleotide moiety, wherein the hydroxy group of the terminal 5'-position of the polynucleotide moiety has been replaced with a thiol group to form the thioether linkage between the polyamide moiety and the polynucleotide moiety; and each of $P^1$, $R$, $R^1$, $R^2$, $R^3$, $R^5$, a, b, c, d, and e is independently those described in the Summary of the Invention section.

Yet another embodiment of the present invention provides a polyamide-polynucleotide primer conjugate of the formula:

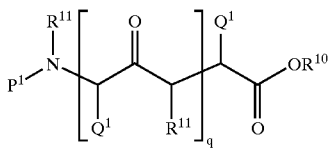

IIB where each $Q^1$ is independently an amino acid side-chain residue or a derivative thereof, provided at least one $Q^1$ is an amino acid side-chain residue derivative of the formula:

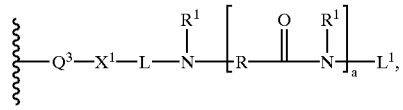

each of the moiety —$Q^3$—$X^1$— is an amino acid side-chain residue having —$X^1$H functional group;

each $X^1$ is independently O, S or $NP^2$;

each $L^1$ is independently H, amide protecting group or a moiety of the formula:

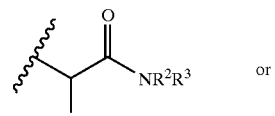 or

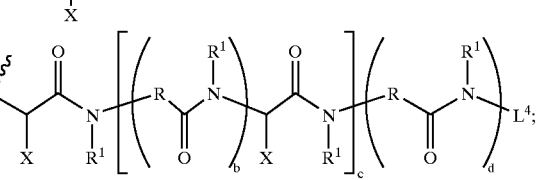

each X is independently an amino acid side-chain residue or a moiety of the formula —$CH_2SL^2$ or —$(CH_2)_3NL^3R^4$;

each $L^2$ is independently a thiol protecting group or a moiety of the formula:

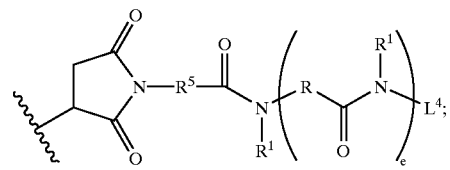

each $L^3$ is independently H, an amine protecting group or a conjugate moiety of the formula:

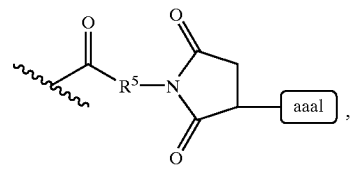

provided one and only one $L^3$ is the conjugate moiety;

each $L^4$ is independently H, amide protecting groups or the moiety of the formula:

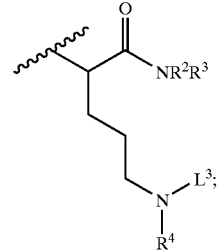

each $R^4$ is independently H, an amine protecting group, or $C_1$–$C_6$ alkyl, provided at least one of $L^3$ or $R^4$ on the same nitrogen atom is not H;

aaa1 is the polynucleotide moiety, wherein the hydroxy group of the terminal 5'-position of the polynucleotide moiety has been replaced with a thiol group to form the thioether linkage between the polyamide moiety and the polynucleotide moiety;

each of L, $P^1$, R, $R^1$, $R^2$, $R^3$, $R^5$, $R_{10}$, $R^{11}$, a, b, c, d, e, and q is independently those described in the Summary of the Invention section.

Figure 4:
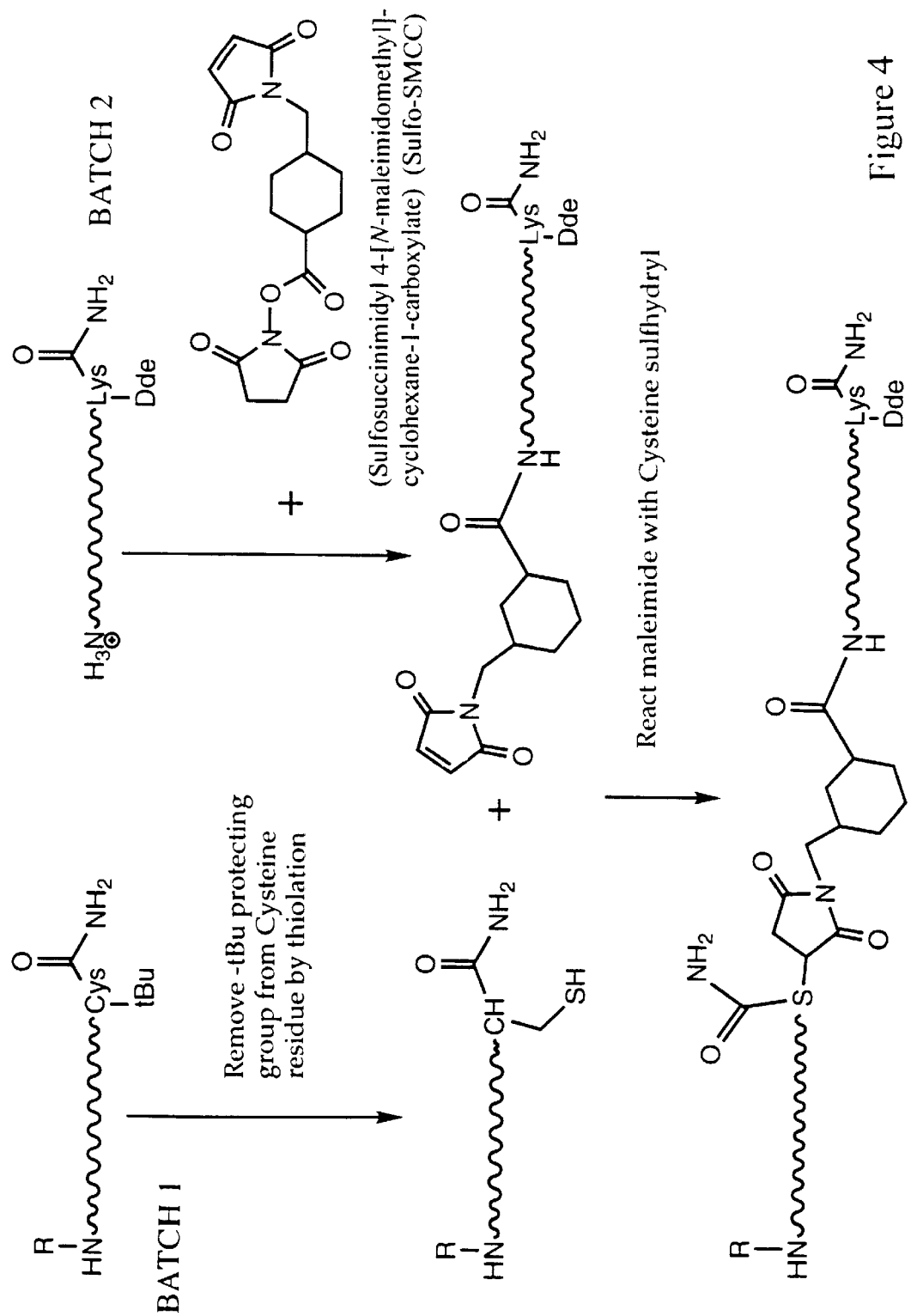
FIG. 4 is a schematic synthetic method for linking two polyamides of the present invention to form a larger polyamide compound.

Polyamides of the present invention can be covalently linked to DNA sequencing primers by, for example, using 5'-thiol terminated primers. FIG. 4 outlines one particular synthetic strategy for high-yield end-to-end linking of two (or more) polypeptoid chains, and high-yield linking of those chains to sequencing primers. As shown in FIG. 4, two batches of long polypeptoids with hydrophilic side chains and different, orthogonally-protected polypeptide residues at their chain termini are prepared. Sulfo-SMCC (sulfosuccinimidyl-4-(N-maleimidomethyl)-cyclohexane-1-carboxylate), which is readily available from Pierce Chemical Company, is then used to couple amines to sulfhydryls in aqueous solution. The first batch of polypeptoids (BATCH 1) contains a terminal cysteine that is protected, e.g., with a tertiary butyl (t-Bu) group. The other batch of polypeptoids (BATCH 2) contains a Dde-protected lysine residue (Dde= 1-(4,4-Dimethyl-2,6-dioxocyclohex-1-ylidene)ethyl) and is terminated with an unsubstituted primary amine. The lysine group, i.e., the amine group in the lysine side-chain, is particularly useful for the coupling of the polyamide to the sequencing primers.

The primary amine terminus of BATCH 2 is reacted with Sulfo-SMCC under standard conditions, attaching a reactive maleimide. This terminal maleimide is then reacted with the sulfhydryl of the deprotected cysteine group on the BATCH 1 peptoids, yielding one, long polypeptoid chain. Reversed-phase HPLC purification can then be used to remove substantially all unreacted precursor chains.

Cysteine monomers with different orthogonal protecting groups are available (e.g., Cys-Sacm, Cys-Tacm, Cys-Trt, Cys-Diphenylmethyl; each of these protecting groups has a different, orthogonal deprotection strategy). A number of other orthogonally-protected lysine residues are also available as sources of amines. The coupling strategy shown in FIG. 4 can be repeated, in such a way that the end-linked dimers can themselves be end-linked, to yield four end-linked 150 mers, etc. By repeating these coupling reactions, polyamides having a desired number of monomers can be readily prepared.

Referring again to FIG. 4, the bifunctional compound Sulfo-SMCC can be used to derivatize a primary amine with a reactive maleimide or other α,β-unsaturated carbonyl compounds, where the amine group is that of the deprotected lysine group on the final linked polypeptoid molecules. This drag-tag primer, i.e., polyamide-polynucleotide primer, coupling reaction can be carried out in an excess of drag-tag, i.e., polyamide, so that virtually every DNA sequencing fragment is linked to a drag-tag. The drag-tag molecules that are not successfully coupled to a primer, i.e., polynucleotide primer, are not electrically charged, nor are they fluorescently labeled; therefore, even if they are present, they do not effect the electrophoretic analysis of the DNA sequencing fragments.

Yet still another embodiment of the present invention provides a method for determining the nucleotide sequence of a target nucleic acid. The method generally involves annealing a polyamide-polynucleotide primer conjugate to the target nucleic acid and extending the primer with a nucleic acid polymerase in the presence of nucleoside triphosphate precursors and at least one chain terminating nucleotide to form conjugated nucleic acid fragments. The conjugated nucleic acid fragments are then separated by electrophoresis in a non-sieving matrix to determine the nucleotide sequence of the target nucleic acid.

In one particular aspect, cycle sequencing protocols for ELFSE samples involve covalently attaching polyamide, preferably polyamides of formula IA or IIA, to the sequencing primers, and taking them through the Sanger cycle sequencing reaction. The sequencing reactions can be prepared using the BigDye Terminator Cycle Sequencing Kit (Perkin Elmer, Foster City, Calif.) and an M13mp18 single-stranded template (New England Biolabs, Beverly, Mass.), with 5'-thiolated M13mp18 universal primers available from Research Genetics (Huntsville, Alam.).

Typically, for high-performance DNA sequencing by capillary electrophoresis, chloride ions, template DNA, and ddNTPs that remain in the sequencing reaction cocktail are removed after the cycle sequencing reactions are complete. This can done by passing the sequencing samples over a series of spin columns using a microcentrifuge, and requires about 30 minutes of work. This cleanup procedure increases the amount of DNA that can be electrokinetically injected into the capillary, and also allows increased read lengths in a given CE separation.

To prepare sequencing samples for high-resolution microchannel electrophoresis, Sanger cycle sequencing extension products can be passed over a set of ultrafiltration spin columns that remove template DNA (Pall Filtron, Inc., Northborough, Mass.), and then over different columns that remove chloride ions, nucleotides, and other buffer components (Centri-Sep Columns, Princeton Separations, Adelphia, N.J.).

Simple capillary electrophoresis experiments can be conducted to identify the best polyamide-based drag-tag and the best polyamide self-assembled monolayer (SAM) microchannel coating, which is discussed in detail below.

The side chains of the polyamides are selected so that they do not prevent DNA chain extension by the polymerase while providing the desired α values of the polyamides. The α value can be accurately determined by carrying out an ELFSE separation of a test sample, recording the peak elution times, calculating the electrophoretic mobilities ($\mu$) of the DT-DNA complexes, and then plotting the data as $1/\mu$ vs. 1/N, where N is number of monomers. The plot yields generally a straight line with a slope of $\alpha/\mu_0$ and a y-intercept of $\mu_0$.

Experiments to determine the best electrophoresis conditions can be carried out using optimized versions of the SAM microchannel wall coatings, discussed in detail below, and polyamide drag-tags.

Preferably, the polyamide-polynucleotide primer conjugate is polyamide-polynucleotide primer conjugate IB or IIB disclosed above.

Still another embodiment of the present invention provides a method for producing a polyamide of the formula:

III

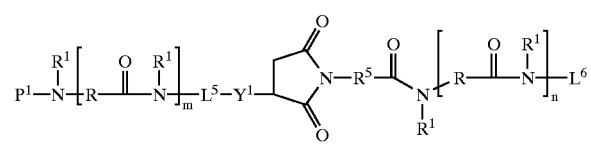

comprising contacting a nucleophilic compound of the formula:

$$\text{P}^1-\text{N}(\text{R}^1)-[\text{R}-\text{C}(=\text{O})-\text{N}(\text{R}^1)]_m-\text{L}^5-\text{Y}^1\text{H} \quad \text{IV}$$

with an α,β-unsaturated carbonyl of the formula:

$$\text{(maleimide)}\text{N}-\text{R}^5-\text{C}(=\text{O})-\text{N}(\text{R}^1)-[\text{R}-\text{C}(=\text{O})-\text{N}(\text{R}^1)]_n-\text{L}^6 \quad \text{V}$$

under conditions sufficient to produce the polyamide III, where $L^5$ is a moiety of the formula:

[structure showing repeating units with subscripts x, y, z and $NR^2R^3$, $R^{13}$]

$L^6$ is a moiety of the formula:

[structure showing repeating units with subscripts s, t, u and $L^4$]

$L^4$ is selected from the group consisting of H, amide protecting group and the moiety of the formula:

[structure with $NR^2R^3$ and X]

each X is independently an amino acid side-chain residue or a moiety of the formula —CH$_2$SL$^2$ or —(CH$_2$)$_3$NL$^3$R$^4$;

each L$^2$ is independently a thiol protecting group or a moiety of the formula:

[succinimide structure with $R^5$, R, $R^1$, $L^4$, subscript e]

each L$^3$ is independently H, an amine protecting group or an α,β-unsaturated carbonyl moiety;

R$^4$ is H, an amine protecting group, or C$_1$–C$_6$ alkyl, provided at least one of L$^3$ and R$^4$ is not H; and each of L, P, P$^1$, P$^2$, R, R$^1$, R$^2$, R$^3$, Y$^1$, a, b, c, d, e, m, n, s, t, u, x, y, and z is independently those described in the Summary of the Invention section.

Yet still another embodiment of the present invention provides a method for producing a polyamide of the formula:

VI

[complex polyamide structure with $R^{11}$, $Q^1$, $Q^3$, $X^1$, L, $OR^{10}$, subscripts $q^1$, $q^2$, $q^3$, $q^4$, a]

comprising contacting a polypeptide of the formula:

VII

[polypeptide structure with $R^{11}$, $Q^1$, $Q^3$, $X^1$, H, $OR^{10}$]

with a polypeptoid of the formula:

VIII $$\text{R}^1-\text{N}(\text{L}^7)-[\text{R}-\text{C}(=\text{O})-\text{N}(\text{R}^1)]_a-\text{L}^1$$

under conditions sufficient to produce polyamide VI, where each R$^{10}$ is independently H or a carboxylic acid protecting group;

each R$^{11}$ is independently H, a protecting group or C$_1$–C$_{10}$ hydrocarbyl;

P$^1$ is H, C$_1$–C$_6$ alkyl or an amine protecting group;

each Q$^1$ is independently an amino acid side-chain residue or a derivative thereof;

each of the moiety —Q$^3$—X$^1$— is an amino acid side-chain residue having —X$^1$H functional group;

each L is a moiety of the formula —C(=O)—R$^{12}$—C(=O)—;

L$^7$ is a moiety of the formula —C(=O)—R$^{12}$—C(=O)OM;

each L$^1$ is independently H, amide protecting group or a moiety of the formula:

[structure with $NR^2R^3$ and X] or

-continued

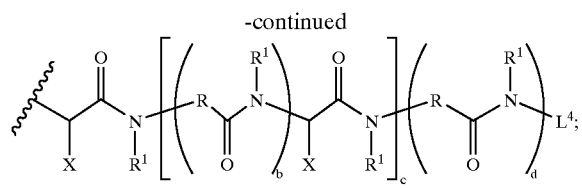

each X is independently an amino acid side-chain residue or a moiety of the formula $-CH_2SL^2$ or $-(CH_2)_3NL^3R^4$;

each $L^2$ is independently a thiol protecting group or a moiety of the formula:

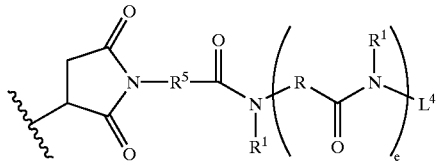

each $L^3$ is independently H, amine protecting groups or an α,β-unsaturated carbonyl moiety;

each $L^4$ is independently H, amide protecting groups or the moiety of the formula:

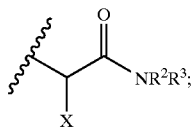

each $R^4$ is independently H, an amine protecting group, or $C_1$–$C_6$ alkyl, provided at least one of $L^3$ or $R^4$ on the same nitrogen atom is not H;

each of M, $P^1$, R, $R^1$, $R^2$, $R^3$, $R^5$, $R^{10}$, $R^{11}$, $R^{12}$, X, a, b, c, d, e, $q^1$, $q^2$, $q^3$, and $q^4$ is independently those described in the Summary of the Invention section.

It is believed that fused silica, such as glass, surfaces are characterized by the low pKa of surface silanol groups. If a tangential electric field is applied to a buffer solution contained in a glass microchannel, then a strong electroosmotic flow in the cathodic direction is produced by the movement of solvated cations residing in the diffuse double layer.

The presence of electroosmotic flow is undesirable for microchannel DNA sequencing, because it reverses the migration order of the DNA peaks (being of greater velocity and opposite directionality to DNA electrophoretic motion) and furthermore because its magnitude is temporally variable and also highly sensitive to the recent chemical history of the glass. Also, the surface of untreated glass is "sticky" onto which proteins and polypeptides can be readily adsorbed. The presence of a passivating polymer or other organic layer eliminates this non-specific adsorption, which typically causes significant band-broadening, and enables high-resolution, long-read-length DNA sequencing separations.

It should be appreciated that it is not necessary to mask the charge of the wall to eliminate electroosmotic flow. Instead, it is simply necessary to make the viscosity within the diffuse double layer essentially infinite. This works because the velocity of: electroosmotic flow is inversely proportional to the viscosity within the diffuse double layer. By covalently bonding a layer of polyamide that has a thickness extending beyond the diffuse double layer to the wall, one makes this regional viscosity virtually infinite, and reduces the electroosmotic flow velocity to a vanishingly small magnitude. This same polyamide layer also functions to physically passivate the glass surface, by preventing the close approach and direct physical adsorption of molecules that are attracted to the negative charge of the surface.

Thus, another embodiment of the present invention provides a material comprising a silanized fused silica and a polyamide, and a method for forming a bond between a fused silica surface and a polyamide comprising:

(a) contacting the surface of the fused silica with an oxidizing agent to form an oxidized surface comprising a hydroxy group;

(b) silanizing the oxidized surface of the fused silica with a silanizing agent to form a silanized surface;

(c) contacting the silanized surface with a linking reagent to form a surface having silanized linker; and (d) contacting the silanized linker with the polyamide to form a covalent bond between the silanized linker and the polyamide.

With respect to the above method for forming a bond between a fused silica surface and a polyamide:

Preferably, the fused silica is glass.

Preferably, the oxidizing agent comprises sulfuric acid, hydrogen peroxide, nitric acid, nitric oxide, chromic acid, mixtures thereof, or the like.

Preferably, the silanizing agent is N-[(trialkoxysily)-alkyl]alkylene diamine, where each alkoxy group of the trialkoxysilyl group and the alkyl groups are independently $C_1$–$C_6$ alkyl and alkylene refers to a $C_1$–$C_6$ alkylene group.

More preferably, the silanizing agent is N-[3-(trimethoxysilyl)-propyl]ethylene diamine.

Preferably, the linking reagent is selected from the group consisting of sulfosuccinimidyl 4-(N-maleimidomethyl) cyclohexane-1-carboxylate and any other reactive compounds containing bifunctional or polyfunctional groups having at least one succinimidyl and at least one maleimidyl moieties.

In one aspect of forming a bond between the fused silica surface and the polyamide, the polyamide is a peptoid of the formula:

IX which forms the covalent bond between the fused silica and the functional group X, where X is $-CH_2SH$ or $-(CH_2)_3NHR^2$; and each of $P^1$, $R^1$, $R^2$, $R^3$, and w is independently those described above.

In another aspect of forming a bond between the fused silica surface and the polyamide, the polyamide is a polypeptide of the formula:

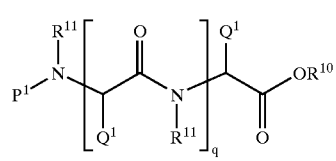

IIC where each $Q^1$ is independently an amino acid side-chain residue or a derivative thereof, provided at least one $Q^1$ is an amino acid side-chain residue derivative of the formula:

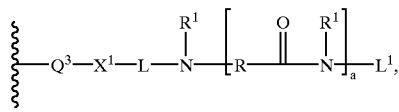

each of the moiety —$Q^3$—$X^1$— is an amino acid side-chain residue having -$X^1$H functional group;
each $L^1$ is independently H, amide protecting group or a moiety of the formula:

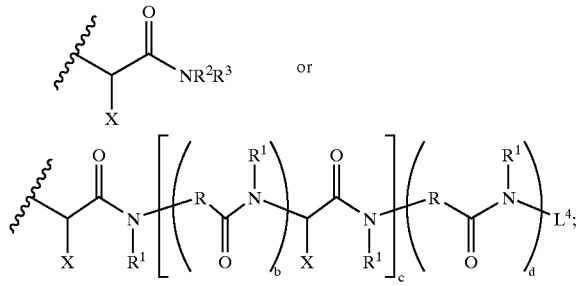

each X is independently an amino acid side-chain residue or a moiety of the formula —$CH_2SL^2$ or —$(CH_2)_3NL^3R^4$;
each $L^2$ is independently a thiol protecting group or a moiety of the formula:

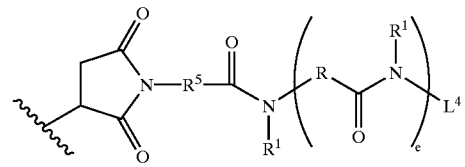

each $L^3$ is independently H, amine protecting groups or an α,β-unsaturated carbonyl moiety;
each $L^4$ is independently H, amide protecting groups or the moiety of the formula:

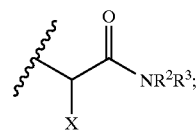

each $R^4$ is independently H, an amine protecting group, or $C_1$–$C_6$ alkyl, provided at least one of $L^3$ or $R^4$ on the same nitrogen atom is not H; and
each of L, $P^1$, R, $R^1$, $R^2$, $R^3$, $R^5$, $R^{10}$, $R^{11}$, $X^1$, a, b, c, d, e, and q is independently those described in the Summary of the Invention section, provided the polypeptide comprises at least one X which forms the covalent bond between the fused silica and the functional group X.

Figure 7A:
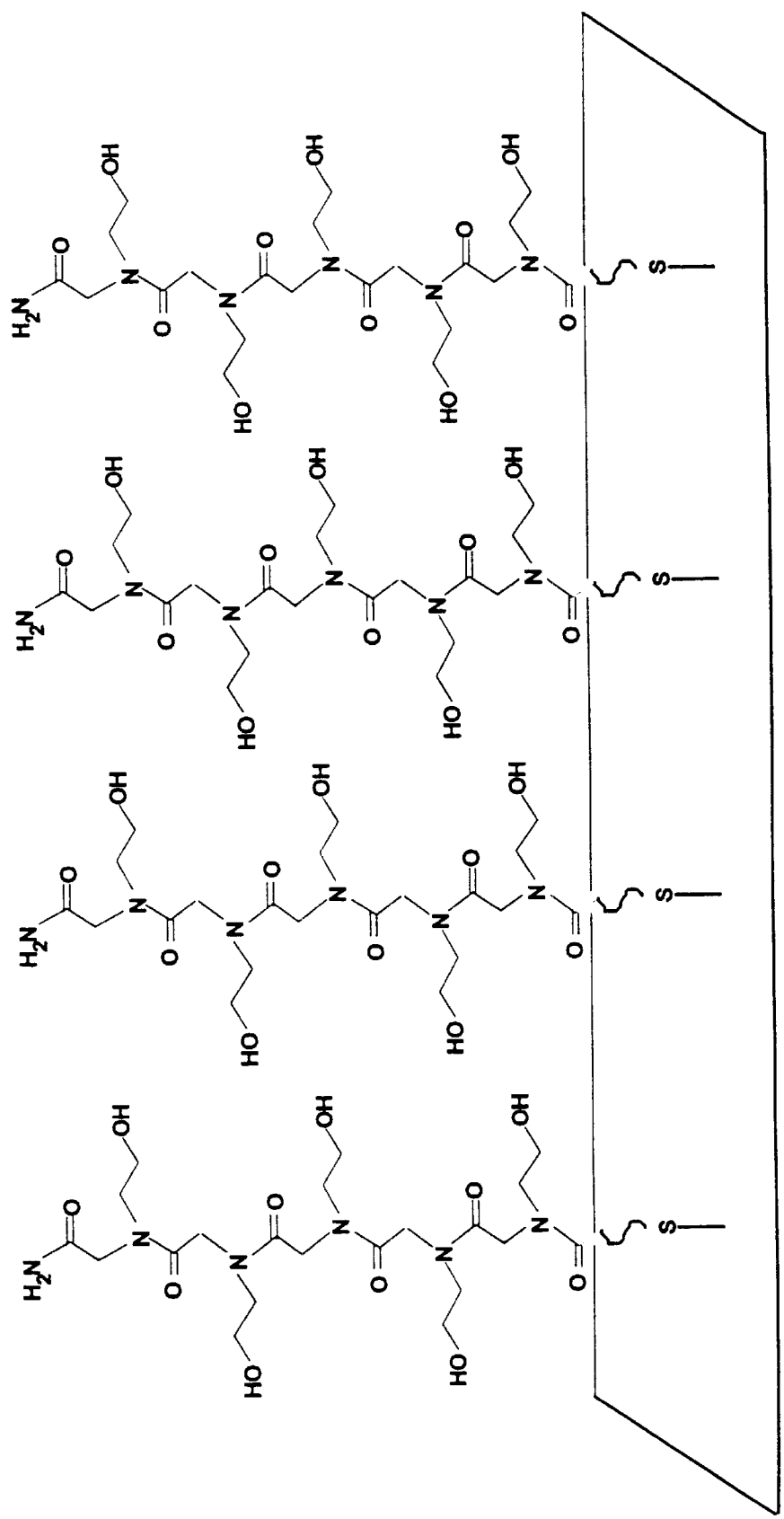
FIGS. 7A and 7B are illustrations of a solid glass surface that is derivatized with a layer of 5-mer and 7-mer polyamides of the present invention, respectively.
Figure 7B:
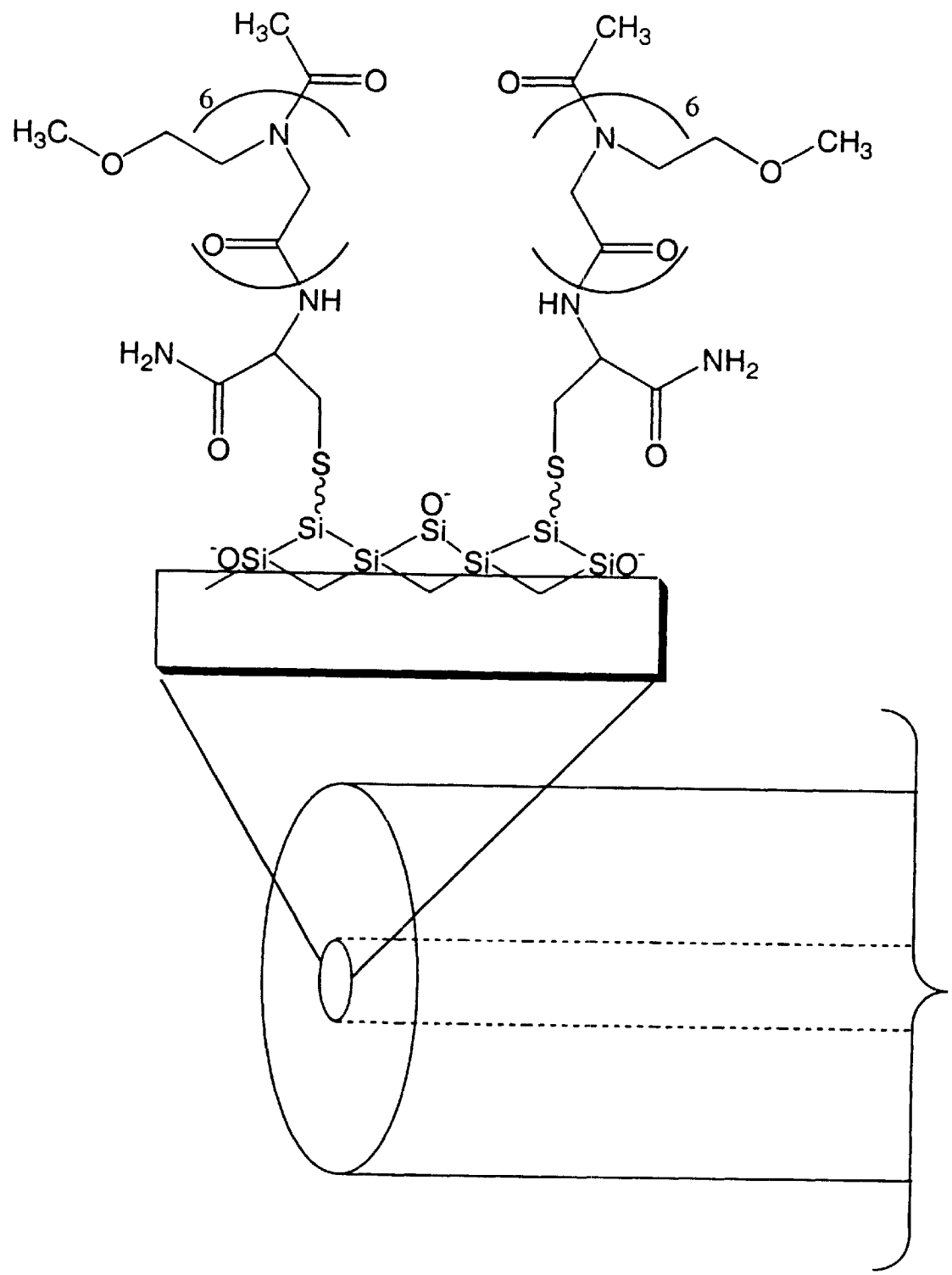

Specifically, the process of wall coating can include the formation of Self-Assembled Monolayers (SAMs) on glass, to coat the glass wall based on polyamides of the present invention that can be tailored for ELFSE separations, for example, See FIGS. 7A and 7B.

The process of the present invention involves derivatizing a glass surface with end-attached polyamides of the present invention. Preferably, polyamides having a reactive functional group, e.g., sulfhydryl (i.e., thiol) or amine, in the terminal group (which is typically provided by the side chain of a cysteine or lysine residue, respectively) are used.

SAM monolayers are both chemically stable and uniform, and obviate the need to force polymer solutions through microchannels to achieve wall coating. Polyamides with hydrophilic side chains such as the one shown in FIG. 3 form excellent microchannel coatings for DNA electrophoresis.

Figure 8:
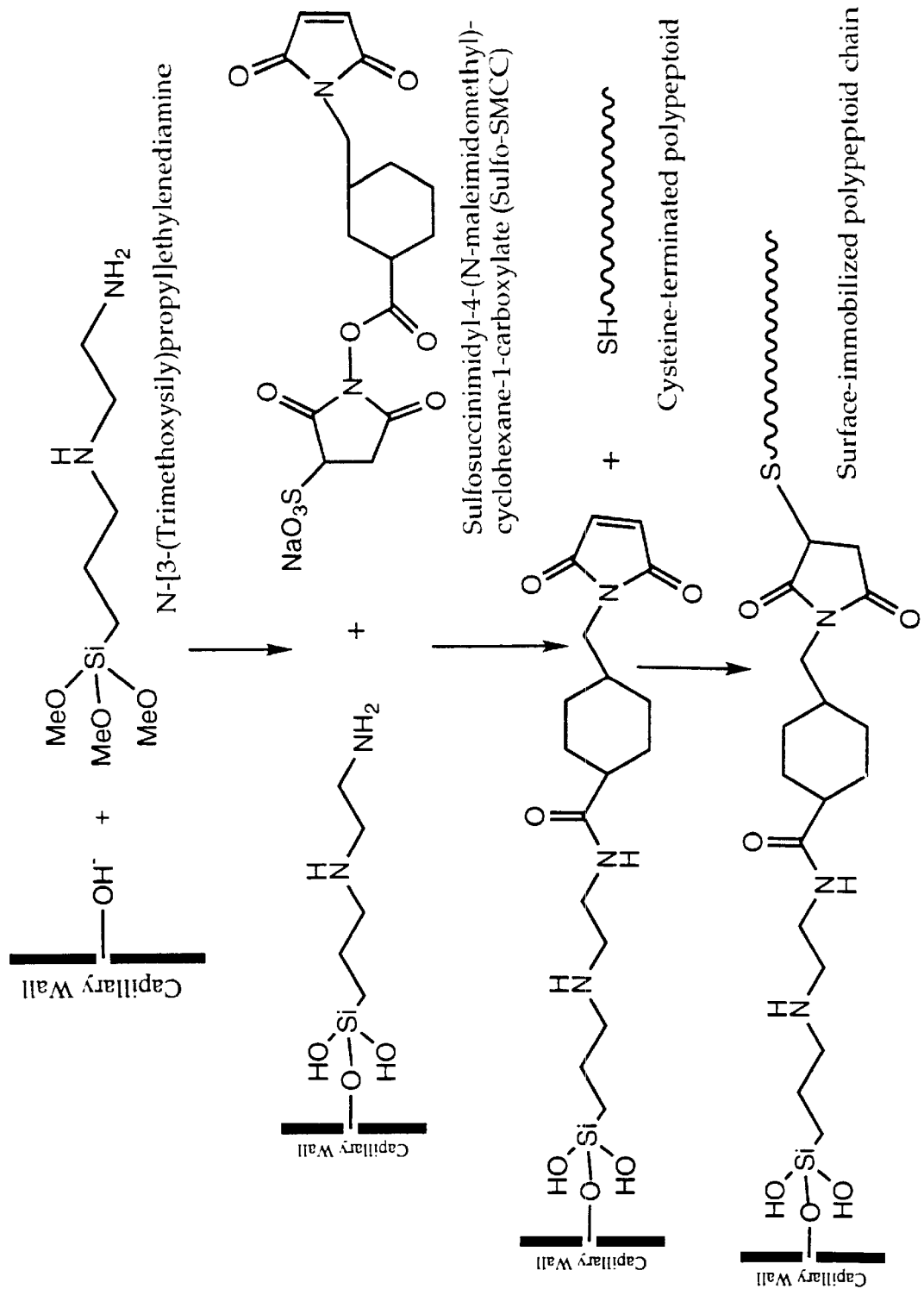
FIG. 8 is a schematic illustration of a synthetic method for covalently bonding polyamides of the present invention onto glass or fused silica surfaces.

One particular process for forming a bond between the fused silica surface and the polyamide is outlined in FIG. 8. Typically, the glass surface is first cleaned to remove both dust and organic materials, and the glass is serially rinsed with water, acetone, and then hexane. Then, the surface is oxidized, e.g., by contacting the glass with a solution of 9:1 (v:v) sulfuric acid and hydrogen peroxide for about 15 minutes. After oxidation, the surface is silanized, for example, by contacting the oxidized surface with a solution comprising 1% N-[3-(trimethoxysilyl)propyl]ethylene diamine, 94% 1 mM acetic acid in methanol, and 5% water. Typically, this silanizing solution is washed over the glass for about 5 minutes. The silanized glass surface is then rinsed with methanol and dried, e.g., for 5 min. at 120° C.

The silanized surface is then derivatized, for example, with SMCC (sulfosuccinimidyl 4-(N-maleimidomethyl) cyclohexane-1-carboxylate), a water-soluble linking reagent that derivatizes amine groups with a reactive maleimide group. Typically, a 0.2 M solution of SMCC is left in the microchannel for about 30 minutes. Following this, the microchannel is successively rinsed with 50 mM sodium borate buffer solution and water. This leaves a maleimide-derivatized surface, which is reactive to sulfhydryl groups. The glass surface, which is typically a microchannel fused silica capillary, is filled with a 160 μM polyamide solution (containing polyamides of the present invention with an unprotected cysteine or lysine terminus) in 0.1 M sodium phosphate buffer (pH 6.6). The microchannel is then rinsed with water, and then it is ready for use, or can be dried and stored indefinitely.

With respect to all of the above compounds discussed above, where appropriate:
Preferably, L is selected from a group consisting of moieties the formula:

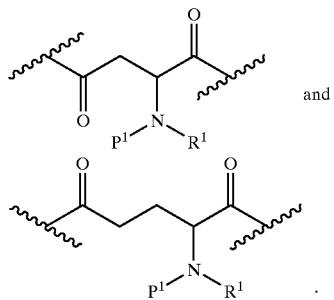

and

Preferably, $L^1$ is a moiety of the formula:

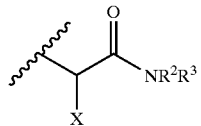

-continued or

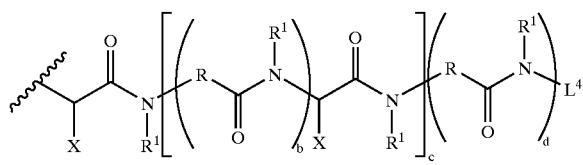

Preferably, $L^2$ is a moiety of the formula:

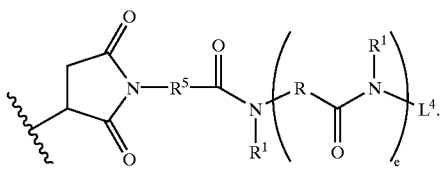

Preferably, when $L^3$ is an α,β-unsaturated carbonyl moiety, the α,β-unsaturated carbonyl moiety is of the formula:

Preferably, $L^4$ is a moiety of the formula:

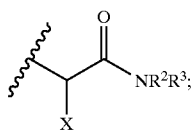

Preferably, at least about 60% of all R is —CH$_2$—, more preferably at least about 75%, still more preferably at least about 90%, and most preferably 100%.

Preferably, when $R^1$ is a hydrophilic $C_1$–$C_{10}$ hydrocarbyl, the hydrophilic $C_1$–$C_{10}$ hydrocarbyl is selected from the group consisting of 2-methoxy ethyl, 2-hydroxy ethyl, 2,2-dimethoxy ethyl, 2-(2'-hydroxy ethoxy)ethyl, 2-[2'-(2"-hydroxy ethoxy)ethoxy]ethyl, and propyl pyrrolidonyl, i.e., a moiety of the formula:

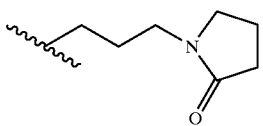

Preferably, $R^2$ and $R^3$ are hydrogen.
Preferably, $R^4$, $R^5$ and $R^6$ are hydrogen.
Preferably, $R^5$ is a moiety of the formula:

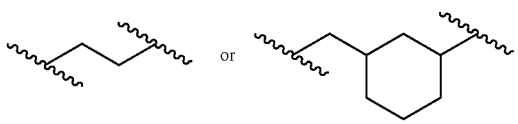

Preferably, $R^{12}$ is methylene or ethylene.
Preferably, $R^{13}$ is methylene or butylene.
Preferably, $P^1$ is hydrogen or acetyl group (—C(=O)CH$_3$).
Preferably, a is an integer from about 1 to about 50; more preferably from about 5 to about 50; and most preferably from about 20 to about 50.
Preferably, b is an integer from about 1 to about 100; more preferably from about 20 to about 100; and most preferably from about 40 to about 100.

Preferably, c is an integer from about 1 to about 10; more preferably from about 4 to about 10; and most preferably from about 6 to about 10.
Preferably, d is an integer from about 1 to about 50; more preferably from about 10 to about 50; and most preferably from about 30 to about 50.
Preferably, $Q^3$ is methylene (from cysteine) or butylene (from lysine).
Preferably, $X^1$ is S or $NP^2$. More preferably $X^1$ is $NP^2$.
Preferably, $P^2$ is independently H or $C_1$–$C_6$ alkyl. More preferably, $P^2$ is H.
Preferably, q is an integer from 1 to about 200, more preferably from about 20 to about 150, and most preferably from about 40 to about 100.
Preferably, q is an integer from 1 to about 30, more preferably from about 5 to about 20, and most preferably from about 7 to about 15.
Preferably, $q^2$ is an integer from 1 to about 10, more preferably from 1 to about 5, and most preferably 1 or 2.
Preferably, $q^3$ is an integer from 1 to about 30, more preferably from about 5 to about 20, and most preferably from about 7 to about 15.
Preferably, $q^4$ is an integer from about 5 to about 75, more preferably from about 15 to about 60, and most preferably from about 25 to about 50.
Preferably, m is an integer from about 10 to about 100, more preferably from about 20 to about 85, and most preferably from about 40 to about 80.
Preferably, n is an integer from about 10 to about 100, more preferably from about 20 to about 85, and most preferably from about 40 to about 80.
Preferably, s is an integer from 1 to about 200, more preferably from about 20 to about 150, and most preferably from about 40 to about 100.
Preferably, t is an integer from 1 to about 10, more preferably from 2 to about 8, and most preferably from 2 to about 6.
Preferably, u is an integer from 1 to about 200, more preferably from about 20 to about 85, and most preferably from about 40 to about 80.
Preferably, x is an integer from 1 to about 200, more preferably from about 20 to about 85, and most preferably from about 40 to about 80.
Preferably, y is an integer from 1 to about 10, more preferably about 2 to about 8, and most preferably from 2 to about 6.
Preferably, z is an integer from 1 to about 200, more preferably from about 20 to about 150, and most preferably from about 40 to about 100.

It should be appreciated that when the same variable occurs more than once in any of the above given formulas, each occurrence of that variable is selected independently.

While polypeptoids, i.e., peptoids, have a number of notable structural features in comparison to polypeptides (see FIG. 1). Peptoids and methods for using a polypeptoid in a variety of applications, including electrophoretic separation of binding polymers, offer a number of advantages. For example, N-substituted polypeptoids lack amide protons; thus, no intra-chain hydrogen-bond network along the polymer backbone chain, which could lead to polymer precipitation from an aqueous solution, is possible, unless hydrogen-bond donating side chains are put in the peptoid chain. In addition, whereas the side chain ("R") groups on biosynthetically produced polypeptides must be chosen from among the 20 amino acids, polypeptoids can include a wide variety of different, non-natural side chains because in peptoid synthesis the R group is introduced as a primary amine (by methods discussed in detail below). This is in contrast to synthetic polypeptides for which the incorporation of non-natural side chains requires the use of non-natural α-protected amino acids. Although a number of unusual amino acid analogs are available from biochemical suppliers such as Novabiochem (La Jolla, Calif.), they are typically much more expensive than the α-protected amino acids for the 20 "natural" protein monomers.

Polypeptoid chains can be synthesized in a sequence-specific fashion using an automated solid-phase protocol, e.g., the sub-monomer synthetic route as disclosed by Zuckermann et al., "Efficient method for the preparation of peptoids [oligo (N-substituted glycines] by submonomer solid-phase synthesis," J. Am. Chem. Soc., 1992, 114, 10646–10647, which is incorporated herein in its entirety. Generally, the sub-monomer synthesis involves derivatizing amide polystyrene microspheres on the solid support (the "resin"), as shown schematically in FIG. 2. Each N-substituted glycine monomer is assembled from two readily available "sub-monomers" in the course of extending the polypeptoid. Hence, polypeptoids can be thought of as alternating condensation copolymers of a haloacetic acid and a primary amine. One particular embodiment of polypeptoid synthesis makes use of α-bromoacetic acid dissolved in dimethylformamide (DMF), e.g., at about 1.2 M concentration. The carboxylic acid group of α-bromoacetyl submonomer is readily activated with neat diisopropylcarbodiimide (DIC) to acylate a resin-bound secondary amino group in high yield, generating an α-bromoacetamide. The side-chain can be introduced as a primary amine (e.g., as a solution of about 1 M in dimethylsulfoxide, i.e., DMSO), which displaces the bromide group in an $S_N2$ fashion to regenerate a secondary amine. Since it is not necessary to work with α-protected monomers, there is no α-deprotection step required in the synthetic protocol. The use of protecting groups is only necessary on chemically-reactive side chains (e.g., hydroxyls, amines, and sulfhydryls, etc.), which typically constitute just a subset of the side chains being incorporated. The use of protecting groups is well known in the art for protecting against undesirable reactions during a synthetic procedure and many such protecting groups are known. See for example, T. H. Greene and P. G. M. Wuts, Protective Groups in Organic Synthesis, 2nd edition, John Wiley & Sons, New York, 1991, which is incorporated herein by reference in its entirety. Exemplary amine protecting groups include, but are not limited to, acyl groups such as an acetyl group and carbamate groups.

Importantly, since there are many hundreds of R—$NH_2$ submonomers readily available at low cost from suppliers such as Aldrich Chemical Co. (Milwaukee, Wis.), peptoid synthesis by the sub-monomer method provides an extremely diverse series of functionalized polypeptoids.

The flexibility of sub-monomer synthesis allows attachment of side chains that satisfy the requirements of specific needs, e.g., hydrophilicity, lack of charge, and lack of a tendency to interact in any significant way with DNA molecules or with the glass walls of the microchannel, if desired.

Another advantage of the polypeptoid synthetic protocol is that it allows easy production of peptoid-peptide chimeras. In a single automated solid-phase protocol, one can alternate the addition of peptoid monomers with the addition of α-Fmoc-protected peptide monomers, the latter added by standard Fmoc coupling protocols employing activating agents such as pybrop or pyBop (i.e., 1H-benzotriazol-1-yloxy-tris(pyrrolidino)phosphonium hexafluorophosphate).

In chemical peptide synthesis, a-protected amino acids are added to the resin-bound chain by the reaction of an activated carboxyl group with a resin-bound primary amine. This reaction can also be accomplished with resin-bound secondary amines, if highly active coupling agents are used. Such incorporation can be affected using a wide variety of orthogonally-protected amino acids, including lysine, cysteine, aspartic acid and/or glutamic acid.

Without being bound by any theory, it is believed that polyamides of the present invention alter the ratio of charge/translational frictional drag (i.e., α value) of binding polymers, thereby allowing separation of binding polymers using an electrophoresis system. It is believed that in the present invention, the charge/translational frictional drag of a binding polymer is altered by attaching to the binding polymer a compound of the present invention, in particular polyamide-polynucleotide primer conjugate of formulas IB and/or IIB, which have a different charge/translational frictional drag than that of the binding polymer. In accordance with the invention, different classes of identically-sized binding polymers can be separated by attaching (i.e., annealing) different polyamide-polynucleotide primer conjugates of the present invention to the binding polymers of each class so that the resulting conjugates of each class have a unique ratio of charge/translational frictional drag.

Conversely, different-sized binding polymers may be separated electrophoretically in a non-sieving liquid medium by annealing substantially identical polyamide-polynucleotide primer conjugates to each size class of binding polymer so that the resultant conjugates of each class have a unique ratio of charge/translational frictional drag in the non-sieving liquid medium. The latter embodiment is particularly applicable for sequencing nucleic acids.

The present invention renders the use of a fixed gel or viscous polymer solution unnecessary for microchannel sequencing, facilitating miniaturization and yielding fast DNA sequencing separations since DNA electrophoretic velocities are much greater in free solution than in gels. Furthermore, the present invention provides read lengths of at least about 250 bases/hour, preferably at least about 400 bases/hour, more preferably at least about 600 bases/hour, still more preferably at least about 1000 bases/hour, and most preferably at least about 2000 bases/hour. Alternatively, methods of the present invention allows read lengths of up to at least about 250 bases, preferably up to at least about 600 bases, more preferably up to at least about 1,200 bases, and more preferably up to at least about 1,500 bases, and most preferably up to at least about 3,000 bases.

Preferably, polyamides of the present invention have at least about 10 monomeric units, more preferably at least about 40 monomeric units, still more preferably at least about 100 monomeric units, even more preferably at least about 500 monomeric units, and most preferably at least about 2000 monomeric units. It should be appreciated that each monomeric unit within the compounds of the present invention can be identical or different.

Preferably, at least about 50% of the amide nitrogens of (N-substituted)polyamides (i.e., polypeptoids) of the present invention are substituted with hydrophilic substituents, more preferably at least about 80%, still more preferably at least about 906, even more preferably at least about 95%, and most preferably at least about 98%. It should be appreciated that each hydrophilic substituent within a polymer can be identical or different.

The present invention provides a method for DNA sequencing that can be carried out in free solution (that is, with no sequencing gel), which is particularly useful in microchannel systems, such as capillary electrophoresis or microchip electrophoresis. This approach is hereinafter referred to as "End-Labeled Free-Solution Electrophoresis" or ELFSE.

At neutral pH, nucleic acid polymers are negatively charged, due to the low pKa of the phosphate groups alternating with base-laden pentose sugars in the polymer backbone. With this negative charge, DNA molecules in aqueous solution migrate toward the positive electrode when placed in a potential field. At steady state, the electrophoretic mobility $\mu$ of DNA is given by the equation:

$$\mu = (q'/f) \tag{1}$$

where q' is the net charge on the molecule and f is the molecular friction coefficient. It has been observed that generally during electrophoresis in free solution, DNA molecules display virtually identical electrophoretic mobilities regardless of their chain length.

While not wishing to be bound by any theory, the present invention is based on a theory that a constant charge-to-friction ratio of DNA that prevents its free-solution separation by electrophoresis could be overcome if one could attach a "perturbing entity," such as a protein, polymer, or microsphere to one or both ends of each DNA chain in a mixture. All that is required of the "end-label" which would allow free-solution separation of DNA is that it has a different charge-to-friction ratio than DNA molecules, and that it be substantially monodisperse. As used in this invention, the term "substantially monodisperse" refers to compounds of the present invention having at least about 90% monodispersity, preferably at least about 95% monodispersity, more preferably at least about 98% monodispersity, and most preferably greater than about 99% monodispersity.

Polyamides of the present invention are not a "label" in the common sense, as they need not be fluorescent or radioactive to provide their function. However, DNA sequencing fragments separated by ELFSE can be conventionally labeled with fluorescent dideoxynucleotide terminators as in standard Sanger cycle sequencing reactions.

By covalently attaching a polyamide of the present invention, i.e., drag-tag, to each DNA molecule in a mixture of Sanger sequencing fragments, a mixture of stable polyamide-polynucleotide primer conjugate complexes (i.e., drag-tag DNA complex or DT-DNA) are formed. If there are no electrostatic and no hydrodynamic interactions that occur between the DNA molecules and the friction-generating drag-tags, then the free-draining behavior of native DNA will be retained in each DT-DNA complex. In that case, the free-solution electrophoretic mobility of a given DT-DNA complex is approximately equal to its overall charge-to-friction ratio (i.e., $\mu = q'/f$, where $\mu$ is the electrophoretic mobility, q' is the net charge on the molecule and f is the molecular friction coefficient).

If N is the number of DNA bases and $\alpha$ is the friction due to the drag-tag expressed in units of the friction, $\xi$, of one DNA base, then the total friction of the DT-DNA complex is given by the product $f = \xi(N+\alpha)$. If the effective charge carried by the drag-tag is defined by $-\beta$, expressed in units of the electric charge, $\rho$, carried by one DNA base (where a negative sign is placed in front of $\beta$ to account for DNA's negative charge), then the total charge carried by the DT-DNA complex is given by $q' = \rho(N-\beta)$. The free-solution mobility of a DT-DNA complex is thus given by the equation $$\mu(N) = \frac{q'}{f} = \frac{\rho(N-\beta)}{\xi(N+\alpha)} = \mu_0 \frac{(N-\beta)}{(N+\alpha)} \tag{1}$$

where $\mu_0 = \rho/\xi$ is the free-solution mobility of a normal free-draining DNA molecule. Equation (1) shows that the electrophoretic mobility of the DT-DNA complexes is dependent on DNA size when $\alpha \neq \beta$, i.e., size separation is possible with drag-tags having a charge-to-friction ratio different than that of DNA. In practice, N>$\beta$ is also desired to ensure that all DNA fragments migrate in the same direction. Optimally, the drag-tag should be neutral, that is, $\beta = 0$. For an uncharged drag-tag, $\beta$ is equal to zero and equation (1) reduces to $$\mu(N) = \mu_0 \frac{N}{(N+\alpha)} \tag{2}$$

In one embodiment of the present invention where drag-tags are hydrophilic but uncharged, to create the maximum driving force for separation, Equation (2) is generally the governing equation for ELFSE, as described by Mayer et al., in "Theory of DNA sequencing using free-solution electrophoresis of DNA-protein complexes," *Anal. Chem.*, 1994, 66, 1777–1780. Therefore, it is preferred to maximize $\alpha$ while also ensuring that the drag-tag fits other necessary criteria.

Experimentally, the value of $\alpha$ can be readily determined by carrying out an ELFSE separation of several different DNA fragments, and making a plot of $1/\mu$ vs. $1/N$, where N is the total number of bases in the chain, i.e., binding polymer. An algebraic rearrangement of Eqn. (2) shows that this should be a straight line with a slope of $\alpha/\mu_0$ and a y-intercept of $1/\mu_0$ (where $\mu_0 = 3.8 \times 10^{-8}$ m$^2$ V$^{-1}$ s$^{-1}$ in a typical electrophoresis buffer and is independent of the applied field strength or DNA size).

In contrast to gel electrophoresis, it is believed DT-DNA complexes that contain longer DNA fragments (with more charged backbone phosphates to provide electrophoretic motive force) pull their drag-tag along at a greater velocity than complexes containing shorter DNA fragments. Hence, the elution order of DNA fragments will be largest-to-smallest if the electrophoresis system has a "race-track" configuration in which all fragments migrate past a single detection window (as in capillary electrophoresis). Alternatively, if the entire separation channel is visualized at once (as on CE microchips), larger DNA fragments will be seen to travel farther in a given period of time. Monotonic size separation of DNA is achievable if each DNA molecule in the mixture carries an identical or highly similar (i.e., at least 95% similarity on molar mass basis) drag-tag.

ELFSE of the present invention is typically carried out in free solution in a microbore fused silica capillary or in a chip microchannel, so a matrix-derived "caging" effect to reduce DNA diffusion is not present. If the injection zone in electrophoresis is made very narrow (1–10 $\mu$m wide) and other contributions to band-broadening are minimized, then for an end-label that generates sufficient drag ($\alpha$=500) and for a 1-meter capillary, one can achieve sequencing read lengths of up to about 3000 bases in less than an hour. A less demanding set of experimental parameters allows one to read about 1600 bases in about 44 minutes or about 1000 bases in under about 30 minutes. It is believed that these very long read lengths are possible because the separation mechanism and the limitations of ELFSE sequencing are fundamentally different from those of gel electrophoresis.

The particular embodiment of preferred drag-tags of the present invention are substantially homogeneous, water-soluble and uncharged. Furthermore, drag-tag moieties of the present invention are designed for covalent attachment to DNA sequencing primers by a high-yielding chemical reaction, have high frictional drag (i. e., a large value of α) and have minimal adsorption or non-specific interaction with the wall of an appropriately-prepared capillary.

The drag-tags of the present invention can be added to the Sanger cocktail before carrying out the cycle sequencing reaction.

As shown in below, the conformation of a drag-tag molecule influences the frictional drag that it provides during electrophoresis.

TABLE 1

Dependence of frictional coefficient f on molecular conformation and molecular mass (M) of the drag-tag

| Molecular Model for Drag-Tag Conformation | Proportionality Relationship |
|---|---|
| Solid sphere | $f \sim M^{0.33}$ |
| Random Coil | $f \sim M^{0.5 \text{ to } 0.6}$ |
| Long Rod | $f \sim M^{0.8}$ |
| Free-Draining Coil | $f \sim M^{1.0}$ |

Table 1 shows that with the exception of the case in which a drag-tag behaves like a free-draining coil, doubling its molecular size will not double the friction (and hence the α value) that it generates. For globular proteins that are essentially spherical in shape, friction (and α) scale is only about 0.33 power of molecular mass. A stiff and hydrophilic drag-tag polymer shows a greater dependence of friction on molecular mass (with an exponent somewhere between 0.6 and 0.8, the exponent for a rod).

Another embodiment of the present invention provides a method for producing polyamides of differing sequences, lengths, and molecular architectures. These monodisperse, water-soluble chain molecules can be covalently attached by chemical means to the 5'-termini of DNA sequencing primers at a single, unique point of attachment. Preferably, each DNA sequencing fragment (i.e., drag-tagged primer) carries a single polyamide of the present invention on its 5'-terminus. The polyamide-labeled sequencing primers (i.e., drag-tagged primers) can be used to carry out cycle sequencing reactions by the method of Sanger, e.g., employing fluorescently-labeled dideoxynucleotide chain terminators.

The resulting single-stranded DNA products of the cycle sequencing reactions are covalently attached to a single polypeptoid drag-tag that is water-soluble, uncharged, and monodisperse, and hence controls the electrophoretic mobility $\mu$ of each (differently-sized and differently-charged) DNA fragment during electrophoresis in such a way that $\mu$ depends monotonically on DNA size. This allows reading of the target nucleic acid sequence. The DNA sequencing fragments, each with their attached polyamide mobility modifiers, can be resolved by automated capillary electrophoresis and/or CE microchip electrophoresis.

Some of the advantages of polyamides of the present invention over currently available water-soluble polymers are listed below. First, polyamides of the present invention can be chemically synthesized in high yields in a sequence- and length-controlled fashion. Polyamides with any one of hundreds of different functionalities in the side chains can be prepared; thus, allowing synthesis of polyamides having a desired physical and chemical properties. Second, polyamides of the present invention can be obtained in relatively high yields and high purity (e.g., at least 50% for a 50 mer and at least 10% for a 120 mer). The purification can be achieved by reversed-phase HPLC to >97% monodispersity. Doubly HPLC-purifying them allows substantially 100% monodispersity of the chains to be used as ELFSE drag-tags. Third, polyamides of the present invention, in particular polypeptoid containing polyamides, are relatively stable in the presence of common proteases; therefore, they have longer shelf-life and aqueous stability than polypeptides. Fourth, two or more long polyamides can be covalently linked together to make a longer chain. Fifth, with a complete control over side chain chemistries polyamides of a wide variety of physical and chemical properties can be prepared, for example, water-soluble, uncharged polyamides that will not significantly interact with DNA, and that will not significantly adsorb on fused silica or glass microchannel surfaces. And sixth, the polyamides of the present invention can be terminated with a chemical linker to allow a covalent attachment of the drag-tags to 5'-thiolated DNA sequencing primers prior to cycle sequencing reactions. Annealing of the primer to the template will still occur in the presence of the attached polyamide.

Particularly preferred hydrophilic substituents in (N-substituted) the polyamide of the present invention include simple methoxy side chains, [N-(3'-aminopropyl) pyrrolidinonyl], ethoxyethanol, 2-ethoxyethyl, acetaldehydedimethylacetal, diethoxyethanol and ethanol. Ethoxyethanol and diethoxyethanol side chains are extremely hydrophilic and bulky. By analogy to hydroxyethyl cellulose polymers, which have an extremely long persistence length in water (80 Å) in comparison to typical random-coil polymers (8 Å), it is believed that polypeptoids with ethoxyethanol and diethoxyethanol side chains can adopt stiff and extended conformations in aqueous solution. An extended molecular conformation is a significant advantage for an ELFSE drag-tag because it increases the dependence of molecular friction coefficient on molecular mass (as shown in Table 1).

EXAMPLES

All of the necessary primary amines (or their precursors) that are needed to introduce the above side chains into polypeptoids via the submonomer synthesis protocol are available from Aldrich Chemical Company (Milwaukee, Wis.) . Solvents and reagents can be purchased from commercial sources and used without further purification.

The terminal hydroxy group of the primary amines, such as ethanolamine and aminoethoxyethanol, is protected during the polypeptoid synthesis with a hydroxy protecting group, e.g., trityl protecting groups, that are easily removed by acidolysis during the trifluoroacetic acid (TFA) cleavage of the polypeptoid from the Rink amide resin after the synthesis is complete.

Example 1

This example illustrates a method for producing polypeptoids and peptide-peptoid chimera on 50 $\mu$mol of Rink amide resin (NovaBiochem, La Jolla, Calif.) having a substitution level of about 0.5 mmol/g.

The Fmoc protecting group is removed by a standard procedure from the resin and the following monomer addition cycle is performed by an automated peptide synthesizer and repeated until the desired sequence is obtained. The resin is bromoacetylated by adding 830 $\mu$L of 1.2 M bromoacetic acid in DMF and 200 $\mu$L of N,N'- diisopropylcarbodiimide (DIC). The mixture is agitated for 40 minutes at 35° C., solvent is removed, and the resulting resin is washed with DMF (4×2 mL). Next, 0.85 mL of a 1 M solution of a primary amine in DMSO is added to introduce the side chain. After the last coupling, the peptoid-resin is cleaved with TFA and then lyophilized. Peptide monomers, which may be included in the sequence, are incorporated using standard Fmoc protocols.

The purity of peptoid/peptide chimera is analyzed by reversed-phase gradient HPLC on $C_{18}$ columns (Vydac, 5 µm, 300 Å, 4.6×250 mm) on a Rainin HPLC dual-pump system (Rainin, Emeryville, Calif.). A linear gradient of 5–95% B in A over 40 min is used at a flow rate of 1 mL/min (solvent A=0.1% trifluoroacetic acid (TFA) in water, solvent B=0.1% TFA in acetonitrile) at a column temperature of 60° C. Preparative HPLC is performed on a Vydac C18 column (15 µm, 300 Å, 10×250 mm) using the same solvent system. Peaks are eluted with a linear gradient of 20–70% B in A over 45 min at a flow rate of 8 mL/min. HPLC fractions are lyophilized, HPLC-analyzed, pooled, and then lyophilized again. Chemical identity and purity is confirmed using an electrospray mass spectrometroscopy.

Example 2

This example illustrate a process for increasing rigidity of a peptoid chain.

The process generally involves, for example, using the procedure of Example 1 while substituting 4-bromomethylphenyl-acetic acid for bromoacetic acid. In this manner, 4-bromomethylphenylacetic acid is incorporated in alternating bromoacetylation steps, or on every third bromoacetylation step in the submonomer protocol of Example 1, depending on the desired rigidity of the peptoid chain.

Process of Example 1 can also be modified to include other chemical strategies for making large-α polyamides. For example, there are many different bifunctional linking reagents available, e.g., from Pierce, and are disclosed by Hermanson, G. T., *Bioconjugate Techniques*, Academic Press, San Diego, 1996, which is incorporated herein in its entirety.

Example 3

This example illustrates a method for producing polypeptoids of various lengths to serve as ELFSE end-labels, i.e., drag-tags.

A set of poly(N-ethoxymethylglycine) homopolymers of 20-, 40-, and 60- monomers in length, with a terminal maleimide functionality, were synthesized on a PE-Biosystems 433A® automated peptide synthesizer by the sub-monomer protocol. Peptoid oligomers were synthesized on 0.1 mmol of Rink amide resin with a substitution of about 0.5 mmol/g. Briefly, after removal of the first Fmoc protecting group from the resin, the following 90-minute monomer addition cycle was performed: The amino-resin was bromoacetylated by adding 4.1 mL of 1.2M bromoacetic acid in dimethylformamide (DMF) plus 1 mL of 1,3-diisopropylcarbodiimide (DIC). This mixture was vortexed in the synthesizer's reaction vessel for 45 minutes, drained, and washed with DMF (4×7 mL). Next, 6 mL of a 1 M solution of the 2-methoxymethylamine in N-methylpyrrolidone (NMP) was added to the resin and agitated for 45 minutes, drained, and washed with DMF (4×7 mL). This process was repeated until the desired number of monomers was added. Finally, 4.1 mL of a solution of 1.2 M maleimidopropionic acid and 1.2M N-hydroxybenzotriazole (HOBT) in DMF was added to the resin along with 1 mL of DIC, and agitated for 45 minutes. The liquid was then drained, and the resin rinsed with dicholoromethane (4×7 mL). Next, the polypeptoid was cleaved from the resin with 95 vol % trifluoroacetic acid in water (1.5 hours at room temperature). The polypeptoid was then removed from the trifluoroacetic acid by a diethylether/water extraction, and the aqueous phase frozen at −85° C. and lyophilized to yield a yellow-gold oil. Crude polypeptoids were dissolved in water and analyzed by reversed-phase HPLC on $C_{18}$ packing (Vydac, 5 µm, 300 Å, 2.1×250 mm).

Preparative HPLC was performed on a Vydac C18 column (Vydac, 15 µm, 300 Å, 22×250 mm) using the same solvent and detection systems; peaks were eluted with a linear gradient of 10–60% B in A over 50 minutes at 12 mL/min. The purified polypeptoids were then analyzed again using the analytical HPLC protocol described above, to ensure the molecules were pure. HPLC chromatograms of crude and purified polypeptoid samples are shown below. After purification, fractions were combined and frozen at −85° C., followed by lyophilization, to yield a clear oil.

Example 4

Figure 5B:
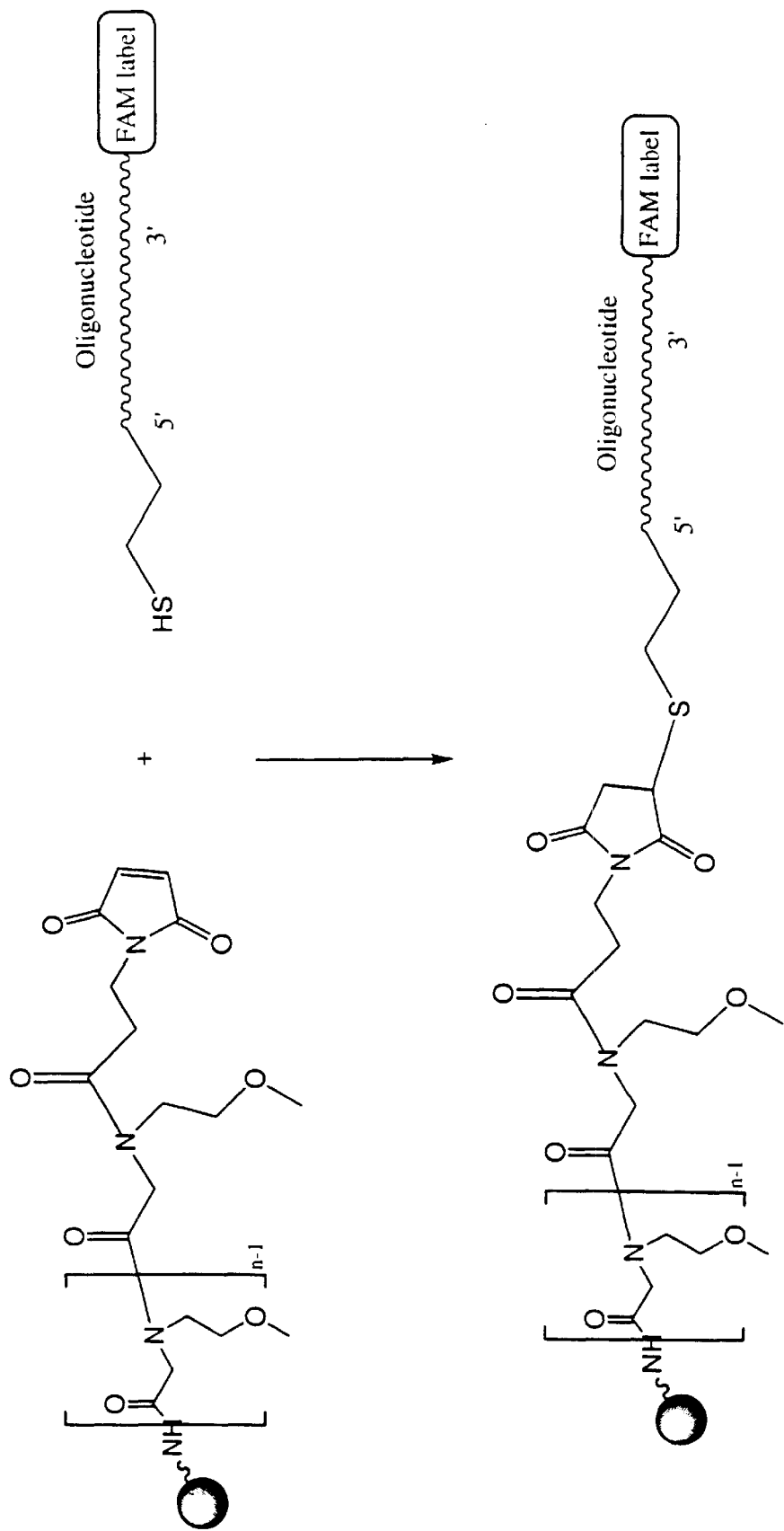
Figure 6:
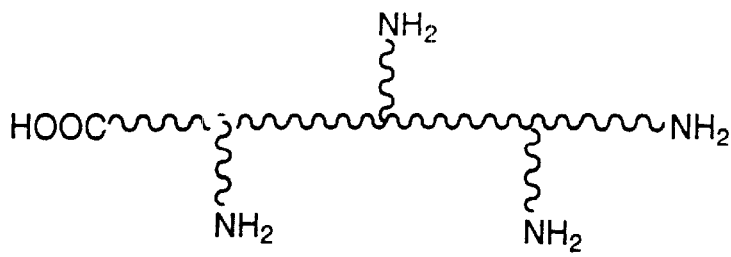
FIG. 6 is a schematic illustration of synthesis of a "bottle-brush" polyamide of the present invention.
Figure 6:
Figure 6:
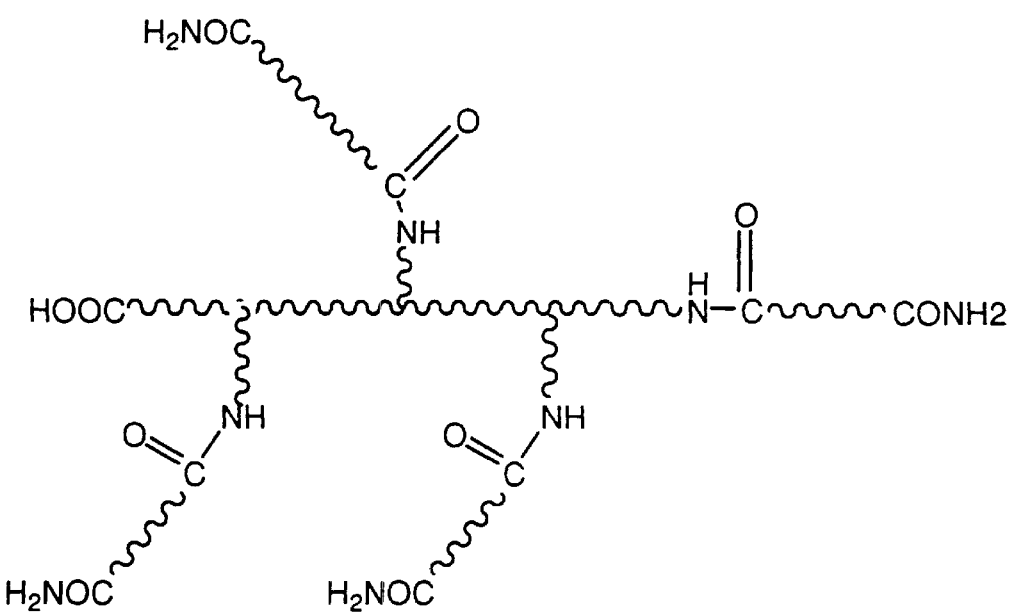

This example illustrates. a method for conjugating a polypeptoid to an oligonucleotide as outlined in FIG. 5B.

A mixture of single-stranded oligonucleotides, 20 and 21 bases in length, having a 5'-C6 thiol modification and 3'-fluorescein (FAM) moiety, were purchased from Oligos, Etc.™ (Wilsonville, Oreg.) and conjugated to the purified polypeptoids via an addition reaction between the 5'-thiol modification of the oligonucleotide and the maleimide functionality of the polypeptoid to yield a stable thioester linkage. To produce the thioester linkage, the oligonucleotide was first chemically reduced to eliminate any intermolecular dimer formation as a result of oxidative linking between the thiols. Reduction was carried out by first dissolving 12.8 nmol of the oligonucleotide in 30 µL of 1× triethylammonium acetate (TEAA) buffer and 4.33 µl of 1M $AgNO_3$ and incubating at 25° C. for 30 minutes. Next, 5.78 µL of 1 M dithiothreitol (DTT) was added and reacted for 5 minutes. The sample was then centrifuged to remove the Ag-DTT precipitate, and the liquid phase was aspirated and placed in a separate tube. The Ag-DTT precipitate was washed twice with 30 µl of TEAA buffer, centrifuged, and all three liquid phases combined. The liquid containing the DNA was then gel-filtered on Centri-Sep columns (Princeton Separations) according to the manufacturer's directions to remove any buffer salts. The eluent from these columns was then immediately frozen in liquid nitrogen and lyophilized. Next, each of the purified peptoids (20-, 40-, and 60- monomers in length from Example 3) was dissolved at a concentration of 12.8 µM in 0.1 M sodium phosphate, 0.15 M NaCl buffer (pH=7.2). A 10 µL aliquot of this solution was then added to the lyophilized DNA from the reduction protocol outlined above, and incubated for 20 hours at room temperature.

Figure 9:
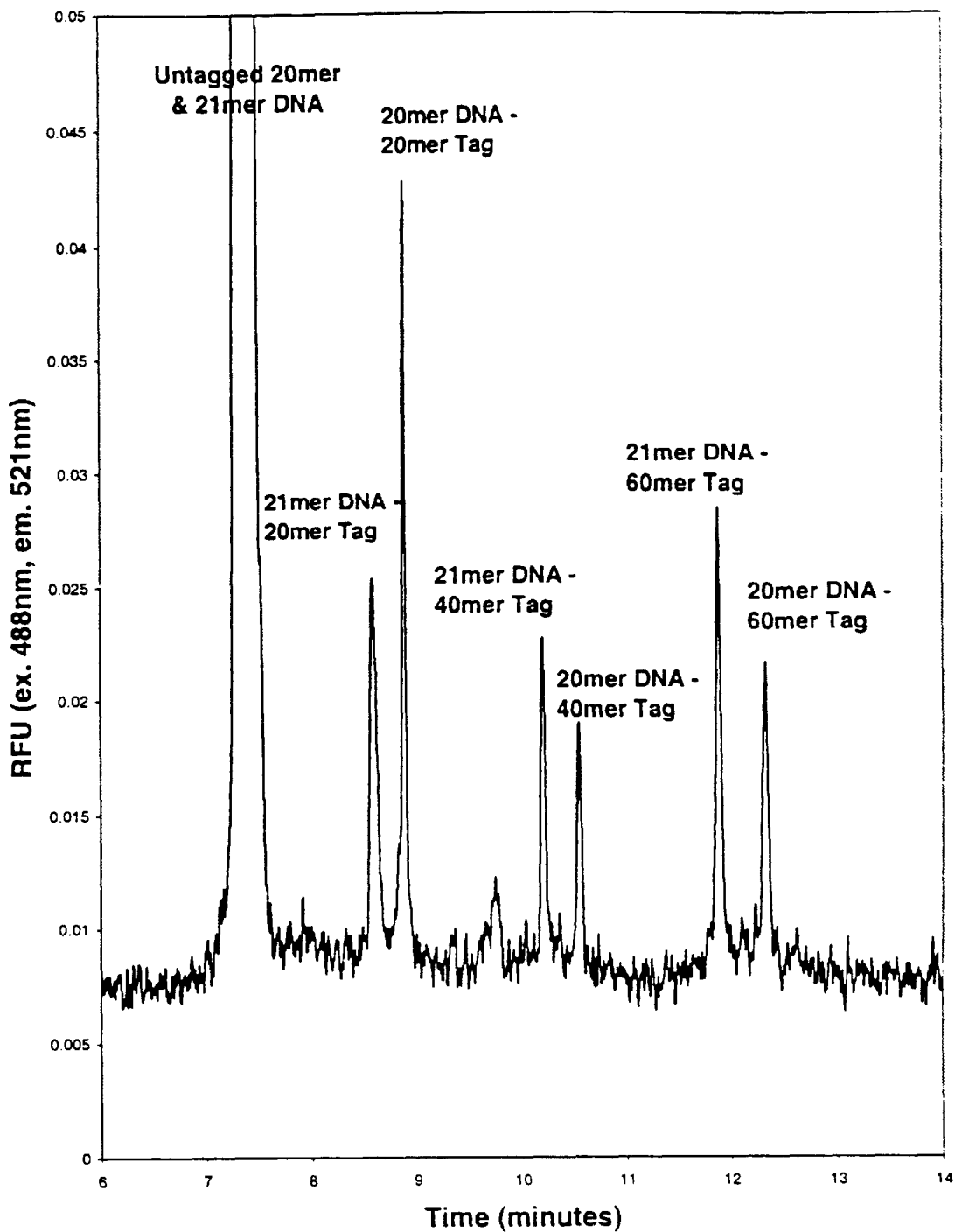
FIG. 9 is a capillary electropherogram of DNA fragments separated by varying lengths of polypeptoid drag-tags as mobility modifiers in the absence of a sieving matrix.

The polypeptoid-oligonucleotide conjugates were analyzed via capillary electrophoresis using a Bio-Rad CE 3000 equipped with a $LIF^2$ laser induced-fluorescence detector. Immediately prior to electrophoresis, aliquots of each of the conjugation reaction above were combined and diluted 1:100 into deionized formamide, heated to 95° C. for 5 minutes, and snap-cooled on ice. Electrophoresis was conducted in fused-silica capillaries 40 cm in length (35.4 cm effective length) and 25 µm in inner diameter. Before each analysis, the capillary was flushed with several column volumes of the running buffer, which was 1× TAPS (pH-adjusted to 8.5 with NaOH), 7M urea, and 0.01% (v/v) POP6 polydimethylacrylamide (PE-Biosystems, Foster City, Calif.). The POP6 polymer in the running buffer serves to 'dynamically coat' the capillary walls and to eliminate electrosmotic flow (EOF) Samples were introduced to the column by an electrokinetic injection of 375 V/cm for 20 seconds, followed by electrophoresis at 375 V/cm for 20 minutes. Detection was accomplished via excitation of the fluorescein label with the 488 nm line of an Ar-Ion laser, with emission detected at 521 nm. As shown in FIG. 9, while untagged 20 mer and 21 mer DNA fragments are not resolved by capillary electrophoresis separation, DNA fragments containing varying lengths of polypeptoid drag-tags are readily separated in the absence of a sieving matrix.

Example 5

This example illustrates free-solution capillary electrophoresis separation of ssDNA fragments labeled with polypeptoid drag-tags of the present invention.

To generate sequencing fragments that are compatible with a single-color electrophoresis instrument, it is necessary to create sequencing fragments that have only one dye type. This can be accomplished by running a Sanger cycle-sequencing reaction in which only one of the four possible dyed-ddNTP terminators is included in the reaction mixture. To accomplish this goal, a 17-base sequencing primer with a 5'-thiol modification was reacted with a 60 mer polypeptoid as described in Example 4 to yield a peptoid-DNA conjugate for use in free solution electrophoresis. The sequence of this primer is such that it would anneal with an M13 ssDNA template. The product of this reaction was then diluted in deionized water to a DNA concentration of 3.02 pmol/µL for use directly in a Sanger cycle-sequencing reaction. 1.05 µL of this conjugate DNA-peptoid sequencing primer was mixed with 1 µL of AmliTap FS DNA polymerase, 4 µl of 5× sequencing buffer, 1 µl of deoxynucleotidetriphosphate mixture, 2 µL of dideoxycytosinetriphosphate-ROX dyed terminator, 0.3 µL of M13 DNA template (0.25 µg/µL stock) (all from PE-Biosystems, Foster City, Calif.) and 10.7 µL of water. This mixture was then subjected to 25 cycles of following thermocycling protocol: denaturation at 96° C. for 30 seconds, annealing at 50° C. for 15 seconds, and extension at 60° C. for 4 minutes. This protocol was followed by a 4° C. hold until the reaction products were ready to be purified. To purify the Sanger cycle sequencing reaction products, the mixture from the thermocycling protocol was gel-filtered using Centri-Sep columns (Princeton Separations, Adelphia, N.J.) according to the manufacturer's directions. This filtered fluid was then dried under vacuum and resuspended in 20 µL of deionized formamide.

Figure 10:
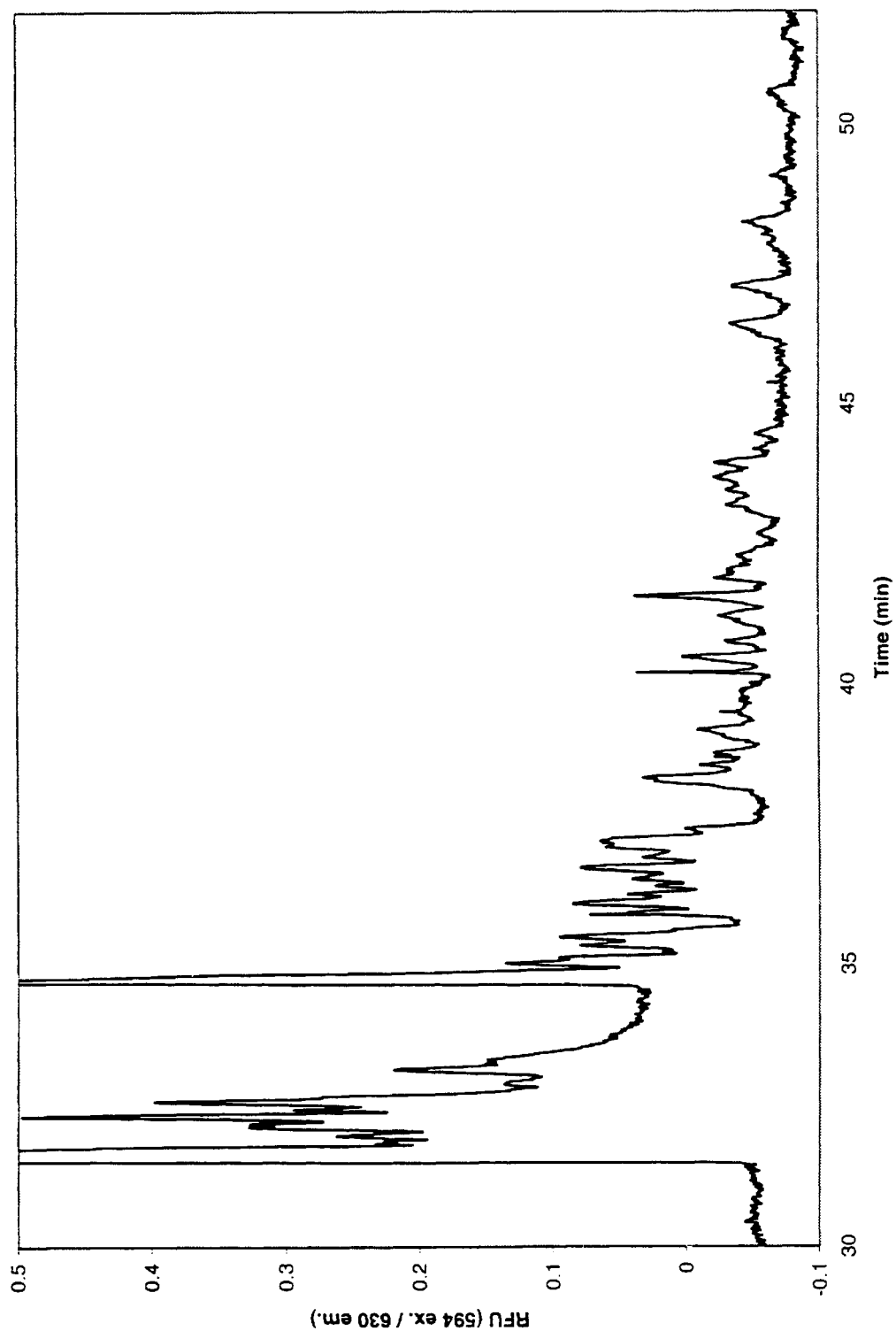
FIG. 10 is a free-solution capillary electropherogram showing separation of ssDNA fragments generated from a one-color Sanger cycle-sequencing reaction which are labeled with polypeptoid drag-tags.

Immediately prior to analysis, the sample in formamide was heated to 95° C. for 5 minutes and snap-cooled on ice. This mixture was then placed in Bio-Rad LIF$^2$ capillary electrophoresis instrument for analysis. The sample was introduced into the capillary with an electrokinetic injection of 300 V/cm for 20 seconds followed by separation at 300 V/cm. The separation required no sieving matrix, only the presence of a buffer of 1× TAPS with 0.0% (v/v) polydimethylacrylamide (PE-Biosystems, Foster City, Calif.). The polydimethylacrylamide served as a dynamic adsorbed coating to eliminate electroosmotic flow, but its concentration is orders-of-magnitude below that needed to allow for gel-based DNA separation. Thus, the polydimethylacrylamide in the electrophoresis buffer does not allow any polymeric-based sieving separation. The capillary was 25 µm in inner diameter and 100 cm in length, using laser induced fluorescence detection with excitation at 594 nm and emission at 630 nm. As shown in FIG. 10, this produced an electropherogram with a large unresolved peak at 32 minutes that represents large unresolved peptoid-DNA sequencing fragments, followed by several peaks that represent smaller sequencing fragments that are well-resolved by ELFSE. The results of this experiment show that we can indeed take a polypeptoid modified DNA primer through a Sanger sequencing reaction and create products that can be separated to read a DNA sequence.

Example 6

This example illustrates a method for internally coating a fused silica capillary with a self-assembled monolayer of oligopeptoid molecules, and the use of this capillary for the electrophoretic separation of double-stranded DNA restriction fragments.

The procedure for preparation of capillaries with an internal coating of a peptoid self-assembled monolayer is outlined in FIG. 8. The capillary was prepared by cutting an appropriate length and 'burning' a window near one of the ends. Then the interior of the capillary was rinsed with each of the following solvents, water, acetone, and hexane for 10 minutes each. The rinsing was accomplished by placing one end of the capillary under vacuum and the submerging the other end in the rinsing solvent. Next, the interior lumen of the capillary was oxidized by rinsing the capillary with 90% (v/v) sulfuric acid in hydrogen peroxide for 15 minutes. This was followed by 1 minute of rinsing with water to flush out any oxidizing reagent. Next the first reactive layer was bonded to the interior surface of the capillary by pumping a solution of 1% N-[3-(Trimethoxysilyl) propyl] ethylenediamine, 94% 1 mM acetic acid in methanol and 5% deionized water for a total of 5 minutes. This was followed by 5 minutes of rinsing with pure methanol and heating in a vacuum oven at 120° C. for 5 minutes. A thiol-reactive layer was bonded to the surface by rinsing a 0.2 mM solution of sulfosuccinimidyl 4-(N-maleimidomethyl) cyclohexane-1-carboxylate solution in 50 mM sodium borate buffer (pH=7.5) for 30 minutes. This was followed by rinsing for 5 minutes with neat sodium borate buffer and then for 5 minutes with deionized water. Finally, the peptoid was bound to the surface by filling the interior lumen of the capillary with a 160 µM solution of peptoid (with an unprotected thiol at the carboxy-terminus) in 0.1 M sodium phosphate buffer (pH=6.6) and incubating the capillary at 4° C. for 20 hours. The capillary was then rinsed with deionized water, dried, and stored in a dessicator until use.

Figure 11:
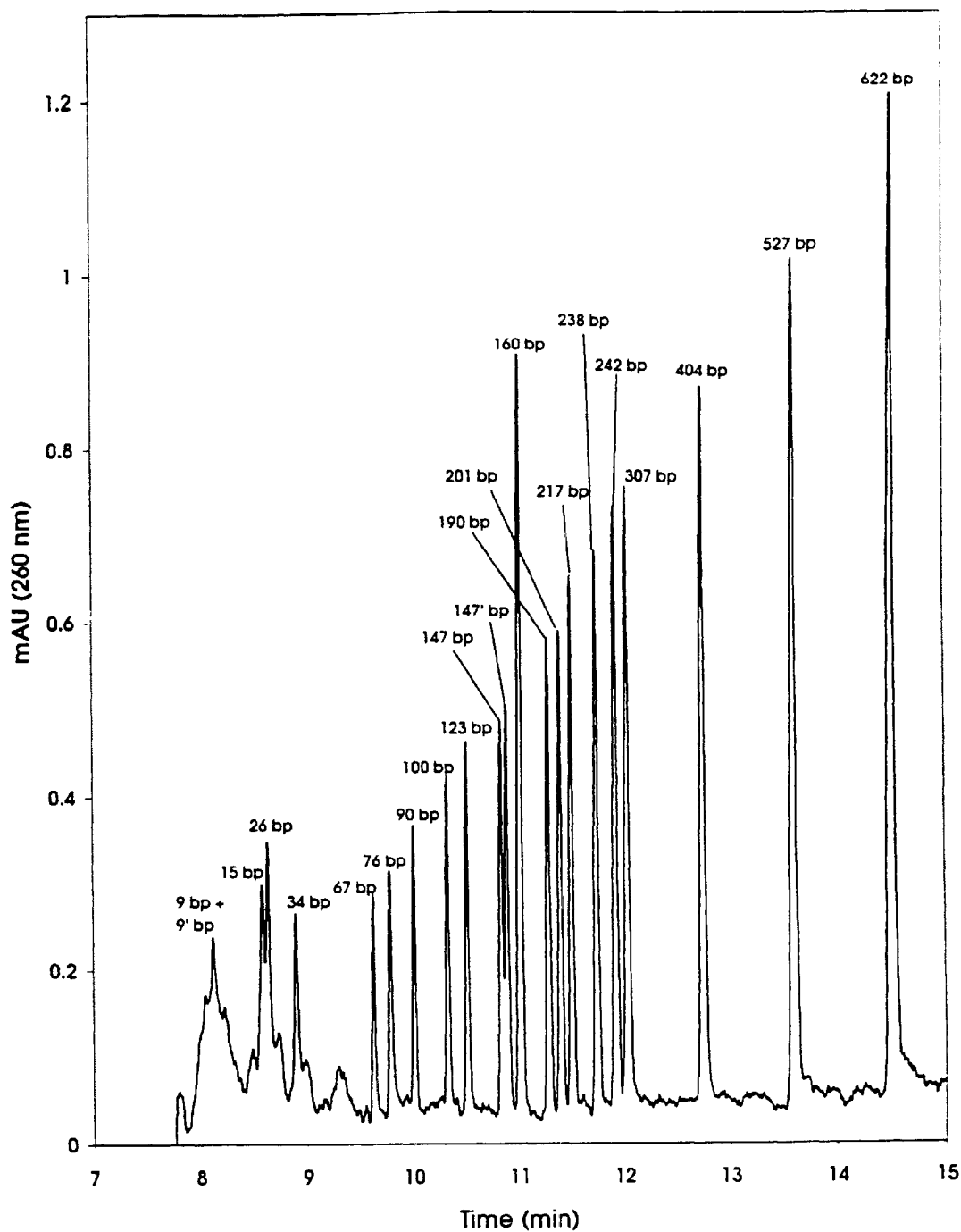
FIG. 11 is a capillary electropherogram of pBR322-Msp I DNA restriction fragments in a fused silica capillary that has been internally coated with an oligopeptide self-assembled monolayer.
Figure 12A:
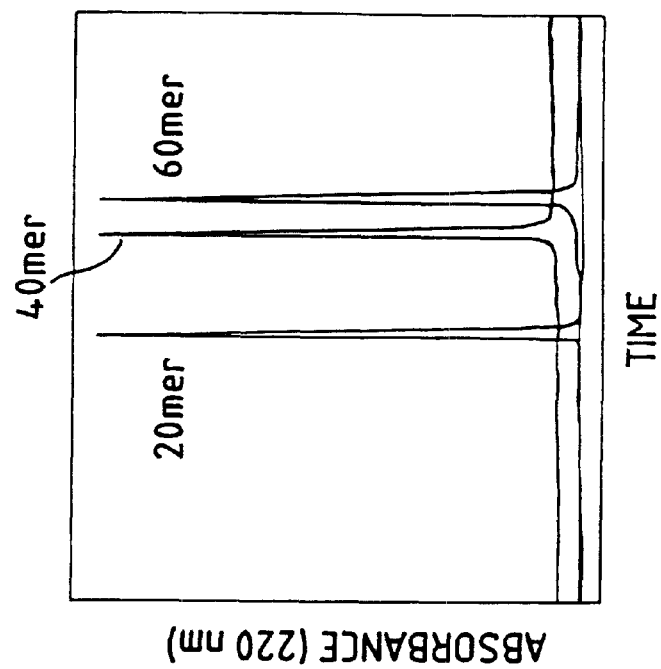
FIG. 12A and FIG. 12B: Analytical reversed-phase HPLC chromatograms of crude and pure polypeptoid synthetic products of a 20 mer, 40 mer, and 60 mer. These molecules were peptoid homopolymers having methoxyethyl sidechains. Gradient HPLC analysis was done at 60° C. on a standard C18 column using water/acetonitrile with 0.1% TFA as the mobile phase (10–60% acetonitrile in water over 50 minutes). The average coupling efficiencies were approximately 99.1%. It was confirmed by electrospray mass spectroscopy that the molar masses of the purified molecules correspond to the calculated masses of the full-length products.
Figure 12B:
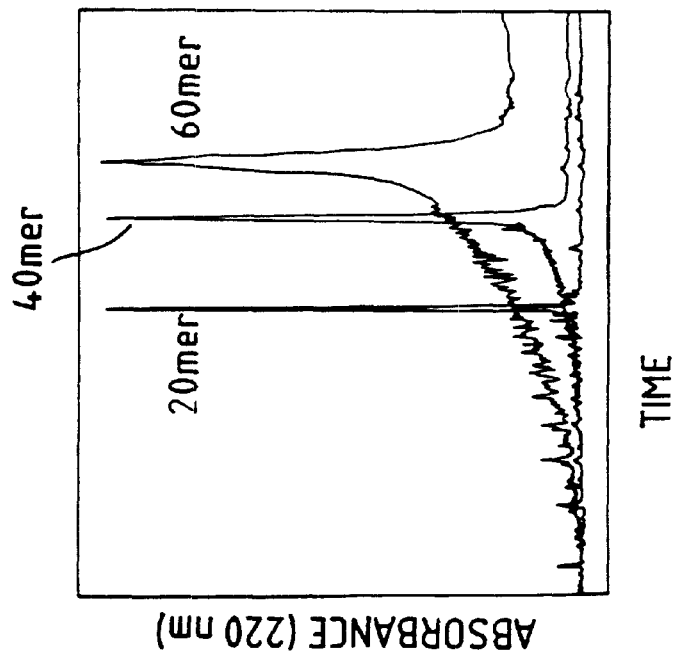

The pBR322-MspI DNA restriction fragments were purchased from New England Biolabs and capillary electrophoresis was conducted in a fused silica capillary that has been internally coated with a monolayer of peptoid hexamers having methoxyethyl sidechains under the following conditions: sieving matrix of 1.5% hydroxypropyl cellulose (HPC), 0.4% hydroxyethyl cellulose (HEC) in 1× TBE; UV detection at 260 nm; 280 V/cm, 9.5 µA; 75 µm i.d., 35 cm total length (31.5 cm to detector). The results are shown in FIG. 11 with each peaks labeled with the number of DNA base pairs present in that particular fragment.

Control experiments were performed in which it was confired that in the absence of the peptoid self-assembled monolayer coating (i.e., in uncoated capillaries), no DNA peaks or separation are obtained under identical experimental conditions. Hence, the peptoid coating enables the high-efficiency DNA separation.

Example 7

This example illustrates a method for assembling synthetic genes encoding protein polymers based on the Seamless cloning technique, i.e., obtaining artificial repetitive polypeptides from bacterial expression.

Using the processes disclosed by McMillan et al., in "Rapid assembly of synthetic genes encoding protein polymers", *Macromolecules*, 1999, 32, 3643–3648; McGrath et al., in "Genetically directed syntheses of new polymeric materials. Expression of artificial genes encoding proteins with repeating -(AlaGly)$_3$ProGluGly- elements", *J. Am. Chem. Soc.*, 1992, 114, 727–733; and Prince et al., in "Constuction, cloning, and expression of synthetic genes encoding spider dragline silk", *Biochemistry*, 1995, 34, 10879–10885, DNA fragments encoding repeating elements were constructed via chemical synthesis and cloning of short oligonucleotides followed by self-ligation. DNA multimers (1460 bp, up to 27 mer) were made by this method and typical yields of purified protein were ca. 10 mg/L of fermentation medium.

Synthetic genes encoding recombinant spider silk proteins was constructed, cloned and expressed. Two restriction enzymes (NheI & SpeI) which have identical cohesive ends but different recognition sites were used for "head-to-tail" orientation and four multimers, ranging in size from 14.7 to 41.3 kDa, were chosen for detailed analysis.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A polyamide comprising at least one hydrophilic $C_1$–$C_{10}$ hydrocarbyl substituent on an amide nitrogen atom, wherein said polyamide comprises a backbone chain having at least one branch chain connected to the backbone chain, wherein said backbone chain is selected form the group consisting of polypeptides, polypeptoids and mixtures therefor, and wherein said branched chain is selected from the group consisting of polypeptoids and peptidepeptoid chimeras, said polyamide having the formula:

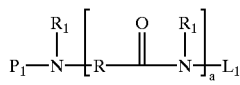

wherein $L^1$ is selected from the group consisting of H, amide protecting groups and moieties of the formula:

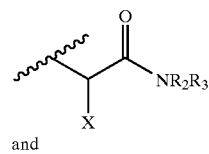

and

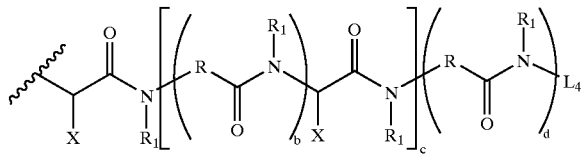

each X is —(CH$_2$)$_3$NL$^3$R$^4$;
each $L^2$ is independently a thiol protecting group or a moiety of the formula:

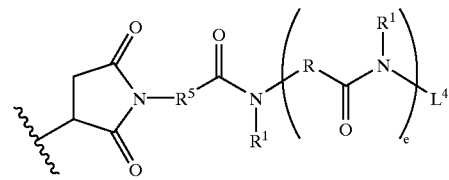

each $L^3$ is independently H, an amine protecting group or an α,β-unsaturated carbonyl moiety, wherein at least one $L^3$ is an α,β-unsaturated carbonyl moiety;
each $L^4$ is independently H, amide protecting groups or the moiety of the formula:

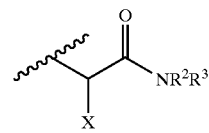

each R is independently —CH$_2$— or

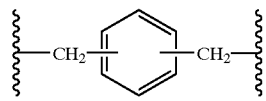

each $R^1$ is independently H, a protecting group or $C_1$–$C_{10}$ hydrocarbyl, provided at least one $R^1$ is hydrophilic $C_1$–$C_{10}$ hydrocarbyl;
each of $R^2$ and $R^3$ are independently H, $C_1$–$C_6$ alkyl, or an amide protecting group;
each $R^4$ is independently H. an amine protecting group, or $C_1$–$C_6$ alkyl, provided at least one of $L^3$ or $R^4$ on the same nitrogen atom is not H;
each $R^5$ is independently $C_1$–$C_{10}$ alkylene;
$P^1$ is H, $C_1$–$C_6$alkyl or an amine protecting group;
a is an integer from 1 to 200;
each b is independently an integer from 1 to 200;
c is an integer from 1 to 10;
d is an integer from 1 to 50; and
each e is independently an integer from 1 to 200.

2. The polyamide of claim 1, wherein at least about 25% of all $R^1$ is hydrophilic $C_1$–$C_{10}$ hydrocarbyl.

3. The polyamide of claim 1, wherein each of said hydrophilic $C_1$–$C_{10}$ hydrocarbyl is independently selected from the group consisting of 2-methoxy ethyl, 2-hydroxy ethyl, 2,2-dimethoxy ethyl, 2-(2'-hydroxy ethoxy)ethyl, 2-[2'-(2"-hydroxy ethoxy)ethoxy]ethyl, and propyl pyrrolidonyl.

4. The polyamide of claim 1, wherein each $R^5$ is independently a moiety of the formula:

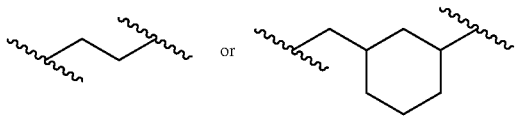

5. The polyamide of claim 1, wherein said α,β-unsaturated carbonyl moiety is of a formula:

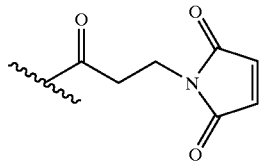

or

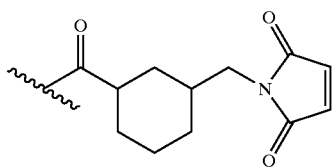

6. A polyamide comprising at least one hydrophilic $C_1$–$C_{10}$ hydrocarbyl substituent on an amide nitrogen atom, having a formula:

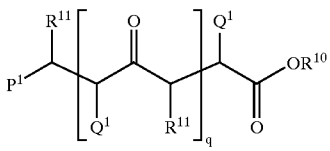

wherein
each $R^{10}$ is independently H or a carboxylic acid protecting group;
each $R^{11}$ is independently H, a protecting group, or $C_1$–$C_{10}$ hydrocarbyl;
q is an integer from 1 to 1,000; and
each $Q^1$ is independently an amino acid side-chain residue or an amino acid side-chain residue derivative, provided at least one $Q^1$ is an amino acid side-chain residue derivative of a formula:

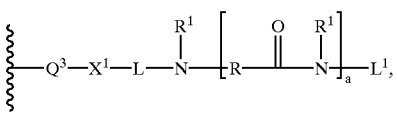

wherein
each of the moiety $Q^3$—$X^1$ is an amino acid side-chain residue having an —$X^1$H Functional group;
each $X^1$ is independently O, S, or $NP^2$;
L is a linker comprising $C_1$–$C_6$ alkylene with carbonyl groups on both of the terminal groups;
each $L^1$ is independently H, amide protecting group, or a moiety of a formula:

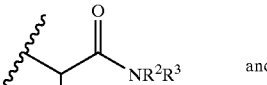
and

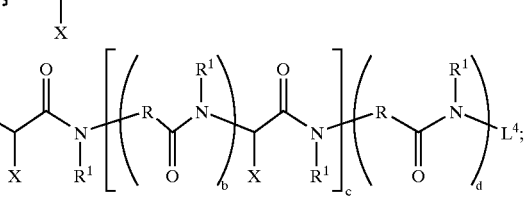

each X is independently an amino acid side-chain residue or a moiety of a formula —$CH_2SL^2$ or —$(CH_2)_3NL^3R^4$;
each $L^2$ is independently a thiol protecting group or a moiety of a formula:

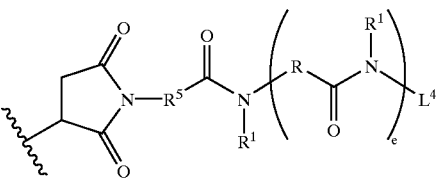

each $L^3$ is independently H, amine protecting group, or an α,β-unsaturated carbonyl moiety;
each $L^4$ is independently H, amide protecting groups, or a moiety of a formula:

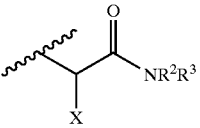

each R is independently —$CH_2$— or

each $R^1$ is independently H, a protecting group, or $C_1$–$C_{10}$ hydrocarbyl;
each of $R^2$ and $R^3$ are independently H, $C_1$–$C_6$ alkyl, or an amide protecting group;
each $R^4$ is independently H, an amine protecting group, or $C_1$–$C_6$ alkyl, provided at least one of $L^3$ or $R^4$ on the same nitrogen atom is different from H;
each $R^5$ is independently $C_1$–$C_{10}$ alkylene;
$P^1$ and $P^2$ is independently H, $C_1$–$C_6$alkyl, or an amine protecting group;
each a is independently an integer from 1 to 200;
each b is independently an integer from 1 to 200;
each c is independently an integer from 1 to 10;
each d is independently an integer from 1 to 50; and
each e is independently an integer from 1 to 200.

7. The polyamide of claim 6, wherein at least one $R^1$ is hydrophilic $C_1$–$C_{10}$ hydrocarbyl.

8. The polyamide of claim 6, wherein at least about 25% of all $R^1$ is hydrophyilic $C_1$–$C_{10}$ hydrocarbyl.

9. The polyamide of claim 8, wherein each of said hydrophilic $C_1$–$C_{10}$ hydrocarbyl is independently selected from the group consisting of 2-methoxy ethyl, 2-hydroxy ethyl, 2,2-dimethoxy ethyl, 2-(2'-hydroxy ethoxy)ethyl, 2-[2'-(2"-hydroxy ethoxy)ethoxy]ethyl, and propyl pyrrolidonyl.

10. The polyamide of claim 6, wherein L is selected from the group consisting of moieties of the formula:

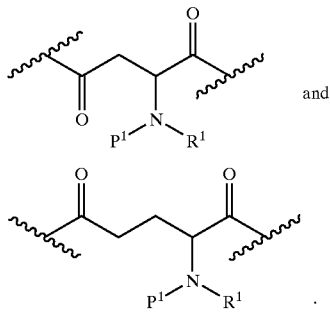

11. The polyamide of claim 10, wherein —$Q^3$—$X^1$— is a moiety of the formula —$(CH_2)_4$—NH—.

12. The polyamide of claim 6, wherein each $R^5$ is independently a moiety of the formula:

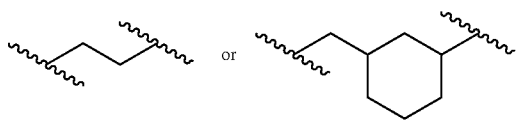

13. The polyamide of claim 6, wherein at least one $L^3$ is an α,β-unsaturated carbonyl moiety.

14. The polyamide of claim 13, wherein said α,β-unsaturated carbonyl moiety is of the formula:

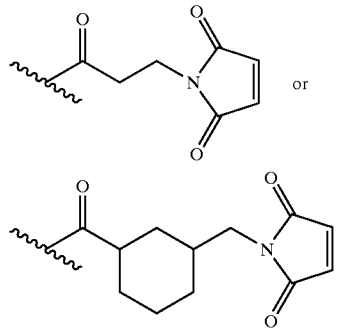

* * * * *

UNITED STATES PATENT AND TRADEMARK OFFICE
CERTIFICATE OF CORRECTION

PATENT NO.   : 6,455,682 B1
DATED        : September 24, 2002
INVENTOR(S)  : Annelise Barron It is certified that error appears in the above-identified patent and that said Letters Patent is hereby corrected as shown below:

Column 37,
Line 56, replace "peptidepeptoid" with -- peptide-peptoid --.

Column 38,
Line 51, replace "H. an" with -- H, an --.

Signed and Sealed this

Eleventh Day of February, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,455,682 B1
DATED        : September 24, 2002
INVENTOR(S)  : Annelise Barron It is certified that error appears in the above-identified patent and that said Letters Patent is hereby corrected as shown below:

Column 38,
Between lines 16-21, please delete

"each $L^2$ is independently a thiol protecting group or a moiety of the formula:

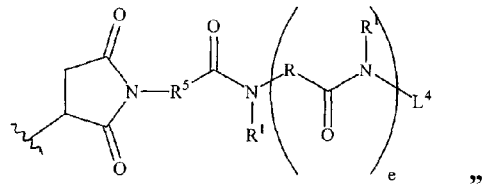

"

Signed and Sealed this

Fourteenth Day of October, 2003

JAMES E. ROGAN
*Director of the United States Patent and Trademark Office*